(12) United States Patent
Olson et al.

(10) Patent No.: US 9,010,605 B2
(45) Date of Patent: Apr. 21, 2015

(54) SLIDING SLEEVE FOR CIRCULAR STAPLING INSTRUMENT RELOADS

(75) Inventors: Lee Ann Olson, Wallingford, CT (US); Patrick Mozdzierz, Glastonbury, CT (US); Scott J. Prior, Shelton, CT (US)

(73) Assignee: Covidien LP, Mansfield, MA (US)

( * ) Notice: Subject to any disclaimer, the term of this patent is extended or adjusted under 35 U.S.C. 154(b) by 635 days.

(21) Appl. No.: 13/348,984

(22) Filed: Jan. 12, 2012

(65) Prior Publication Data

US 2013/0181036 A1    Jul. 18, 2013

(51) Int. Cl.
*A61B 17/068* (2006.01)
*A61B 17/115* (2006.01)

(52) U.S. Cl.
CPC ............. *A61B 17/068* (2013.01); *A61B 17/115* (2013.01)

(58) Field of Classification Search
CPC ............... A61B 17/068; A61B 17/115; A61B 17/1155; A61B 2017/07214; A61B 2017/07257
USPC ..................... 227/175.1, 176.1, 180.1, 175.2; 606/219
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |

(Continued)

FOREIGN PATENT DOCUMENTS

| CA | 908529 A | 8/1972 |
|---|---|---|
| CA | 1 136 020 A1 | 11/1982 |

(Continued)

*Primary Examiner* — Michelle Lopez

(57) ABSTRACT

A surgical stapling device and method for joining tissue portions are provided including a handle assembly, an elongate body extending from the handle assembly, a cartridge assembly supported on a distal end of the elongate body, and an anvil assembly at a distal end of the surgical stapling device. The anvil assembly includes a shaft for removably coupling the anvil assembly to the cartridge assembly and a head pivotally mounted to a distal end of the shaft. A sleeve member is slidably disposed about the shaft of the anvil assembly and is transitionable between a first position, where the sleeve member engages the head of the anvil assembly to secure the head in an un-tilted condition, and a second position, where the sleeve member is disengaged from the head of the anvil assembly to allow the head to tilt.

13 Claims, 28 Drawing Sheets

(56) References Cited

U.S. PATENT DOCUMENTS

| | | |
|---|---|---|
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |

(56) References Cited

U.S. PATENT DOCUMENTS

| | | |
|---|---|---|
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Fuchs et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |

(56) References Cited

U.S. PATENT DOCUMENTS

| | | |
|---|---|---|
| 8,066,169 B2 | 11/2011 | Viola |
| 8,070,035 B2 | 12/2011 | Holsten et al. |
| 8,070,037 B2 | 12/2011 | Csiky et al. |
| 2003/0111507 A1 | 6/2003 | Nunez |
| 2005/0051597 A1 | 3/2005 | Tolendano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0144897 A1 | 7/2006 | Jankowski et al. |
| 2006/0201989 A1 | 9/2006 | Ojeda |
| 2006/0241692 A1 | 10/2006 | McGuckin, Jr. et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1354560 A3 | 4/2004 |
| GB | 1185292 A | 3/1970 |
| GB | 2016991 A | 9/1979 |
| GB | 2070499 A | 9/1981 |
| WO | WO 8706448 A | 11/1987 |
| WO | WO 8900406 A1 | 1/1989 |
| WO | WO 9006085 A1 | 6/1990 |

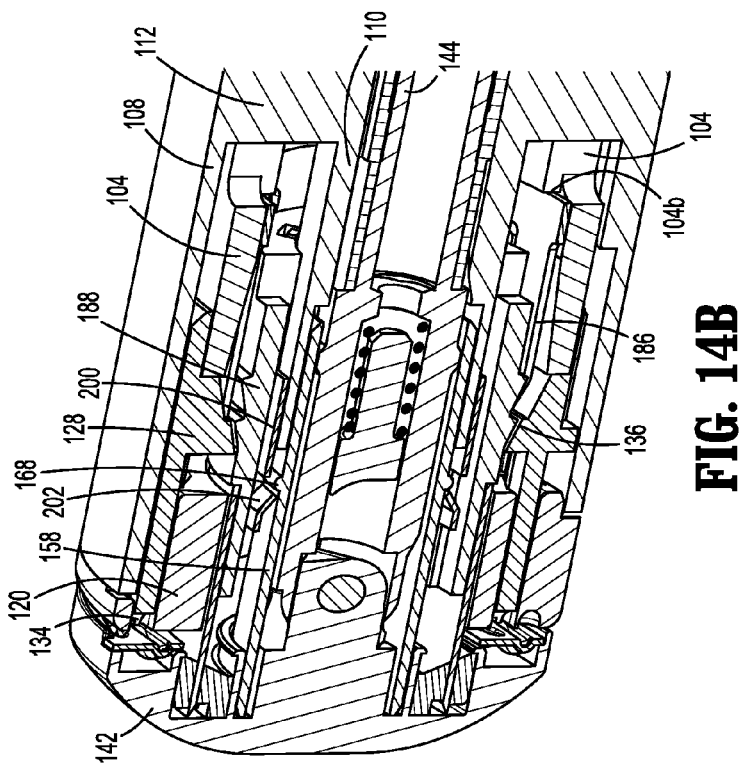
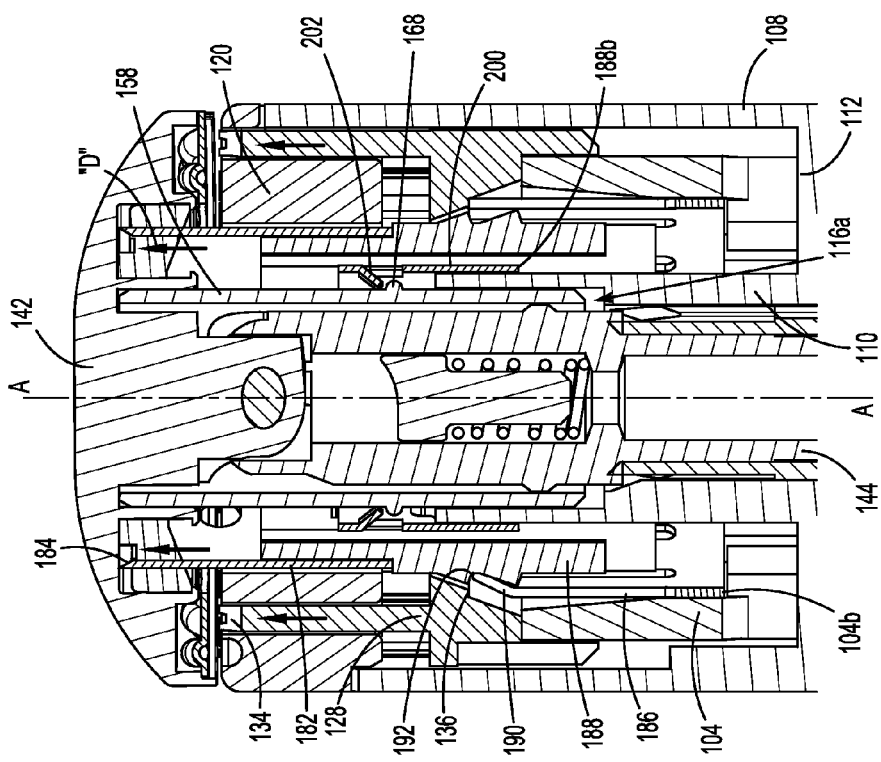

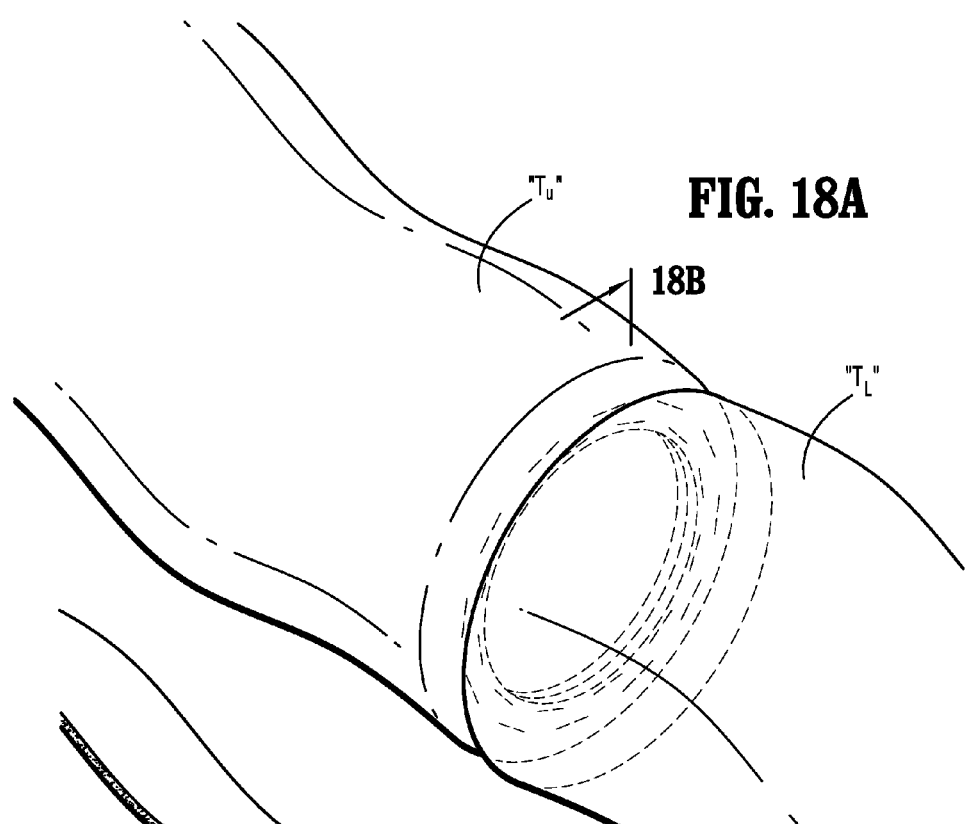
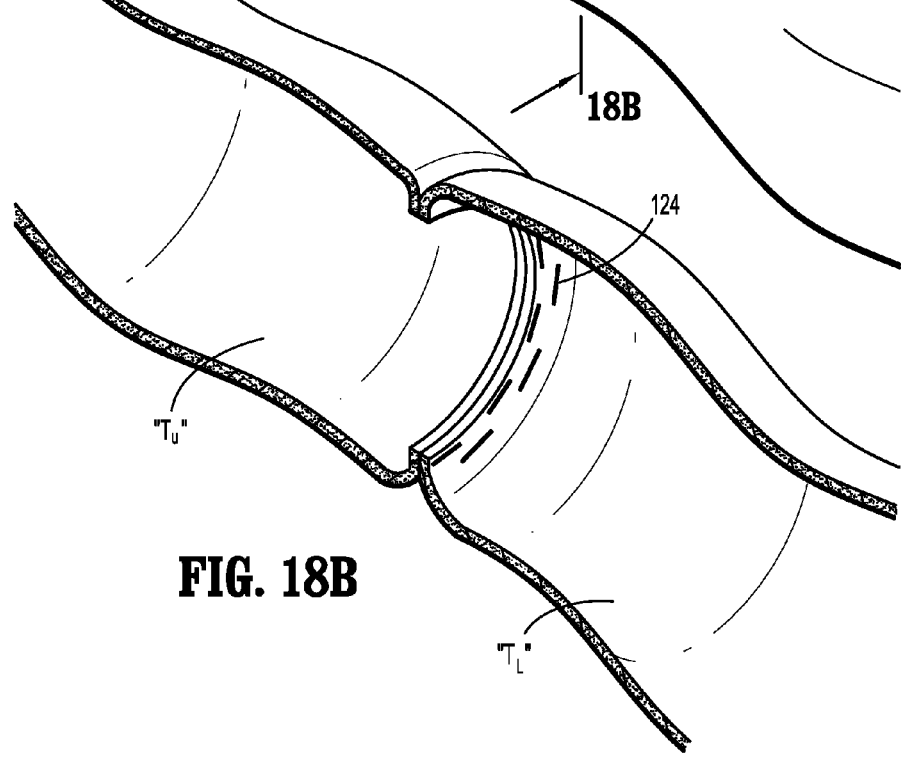

SLIDING SLEEVE FOR CIRCULAR STAPLING INSTRUMENT RELOADS

BACKGROUND

1. Technical Field

The present disclosure relates to surgical instrumentation for performing a surgical procedure. More particularly, the present disclosure relates to circular stapling instruments.

2. Background of Related Art

Circular staplers are known, as are their use in procedures in which the stapler is inserted through natural body orifices. Generally, circular staplers are used to provide an anastomosis between two body vessels. Typically the circular staplers include a cartridge assembly on a distal end of an elongate body. The cartridge assembly includes a mechanism for forming staples and a knife for cutting the stapled tissue. Actuation of the cartridge assembly may be performed by a manually operated trigger or a powered drive assembly. Generally, both the actuation of the staple forming mechanism and the advancement of the knife occur at the same time, i.e., simultaneously. Thus, the force provided by the actuation assembly must be sufficient to overcome the force required to form the staples and the force required to advance the knife through the tissue being stapled. Further, the simultaneous actuation of the staple forming mechanism and advancement of the knife requires that the staple forming mechanism and the knife travel the same distance, thereby limiting the staple formation height to the knife travel distance.

Circular staplers which include an anvil assembly having a tilt-able anvil head are well known in the art. In some known circular staplers, tilting anvil mechanisms are spring loaded to tilt to a maximum angle allowed by the circular stapler and/or anvil geometry. Tilting the anvil head to its maximum angle facilitates pulling the anvil head through the area in which the body vessels have been joined in an anastomosis ring.

In forming the anastomosis, the knife of the circular stapler cuts away a donut of tissue. In certain instances, however, the anastomosis donut, the remaining tissue severed from the anastomosis by an annular knife, may become pinched by the anvil head when the anvil head is tilted and thus inhibit full tilting of the anvil head. As a result, the anvil head may contact an edge of the anastomosis ring during withdrawal, which, in turn, may cause unwanted tissue damage (i.e., damage to the anastomosis ring) and/or may result in higher retraction forces being necessary during removal of the anvil head through the anastomosis ring.

Therefore, it would be beneficial to have a circular stapler including a cartridge assembly configured to form staples independently of cutting tissue. It is also desirable to retain the anastomosis donut in a manner that avoids interference between the anvil head of the stapler and donut.

SUMMARY

Accordingly, a surgical stapling device for joining tissue portions is provided including a handle assembly, an elongate body extending from the handle assembly, a cartridge assembly supported on a distal end of the elongate body, and an anvil assembly at a distal end of the surgical stapling device. The cartridge assembly includes a staple cartridge containing a plurality of surgical staples in an annular array. The anvil assembly includes a shaft for removably coupling the anvil assembly to the cartridge assembly and a head pivotally mounted to a distal end of the shaft. The anvil assembly is translatable relative to the cartridge assembly between a first position, where the anvil assembly is spaced from the cartridge assembly, and a second position, where the anvil assembly is approximated relative to the cartridge assembly for clamping tissue therebetween. The head of the anvil assembly is transitionable between a first condition, where a tissue contacting surface of the head is substantially perpendicular to the shaft, and a second condition, where the tissue contacting surface of the head is tilted relative to the shaft. A sleeve member is slidably disposed about the shaft of the anvil assembly and is transitionable between a first position, where the sleeve member engages the head of the anvil assembly to secure the head in the first condition, and a second position, where the sleeve member is disengaged from the head of the anvil assembly to allow the head to transition to the second condition.

In one aspect, a distal end portion of the sleeve member is insertable into a recess of the head of the anvil to removably couple the sleeve member to the anvil assembly and secure the head in the first condition.

In one aspect, the cartridge assembly includes a locking member that is translatable relative to the sleeve member to engage a protrusion of the sleeve member when the anvil assembly is in the second position. The locking member is configured to axially maintain the sleeve member relative to the cartridge assembly and to disengage the sleeve member from the head of the anvil assembly when the anvil assembly transitions from the second position to the first position.

In one aspect, the cartridge assembly includes a knife carrier that is translatable relative to the cartridge assembly to engage and translate the locking member relative to the sleeve member.

In one aspect, the cartridge assembly includes a knife pusher that is configured to engage a lip of the knife carrier and is translatable relative to the cartridge assembly to translate the knife carrier relative to the cartridge assembly.

In one aspect, the knife pusher is configured to translate relative to the cartridge assembly during actuation of a first stroke of the surgical stapling device, with the knife pusher disengaged from the lip of the knife carrier, and configured to translate relative to the cartridge assembly during actuation of a second stroke of the surgical stapling device, with the knife pusher engaged with the lip of the knife carrier, to thereby translate the knife carrier relative to the cartridge assembly during the second stroke.

In one aspect, the sleeve member is configured to retain a severed donut of tissue thereabout after actuation of the surgical stapling device.

In another aspect, a surgical stapling device for joining tissue portions is provided including a handle assembly, an elongate body extending from the handle assembly, a cartridge assembly supported on a distal end of the elongate body, and an anvil assembly at a distal end of the surgical stapling device. The cartridge assembly includes a staple cartridge containing a plurality of surgical staples in an annular array. The anvil assembly includes a shaft for removably coupling the anvil assembly to the cartridge assembly and a head pivotally mounted to a distal end of the shaft. The anvil assembly is translatable relative to the cartridge assembly between a first position, where the anvil assembly is spaced from the cartridge assembly, and a second position, where the anvil assembly is approximated relative to the cartridge assembly for clamping tissue therebetween. The head of the anvil assembly is transitionable between a first condition, where a tissue contacting surface of the head is substantially perpendicular to the shaft, and a second condition, where the tissue contacting surface of the head is tilted relative to the shaft. A staple pusher is slidably disposed within the cartridge assembly and is configured to translate relative to the cartridge assembly to engage the plurality of surgical staples and to urge the plurality of surgical staples towards the anvil assembly. A sleeve member is slidably disposed about the shaft of the anvil assembly and is transitionable between a first position, where the sleeve member engages the head of the anvil assembly to secure the head in the first condition, and a second position, where the sleeve member is disengaged from the head of the anvil assembly to allow the head to transition to the second condition. A locking member is slidably disposed within the cartridge assembly and is translatable relative to the sleeve member upon translation of the staple pusher relative to the cartridge assembly. The locking member is configured to engage the sleeve member to axially maintain the sleeve member relative to the cartridge assembly and to disengage the sleeve member from the head of the anvil assembly when the anvil assembly transitions from the second position to the first position.

In one aspect, a proximal end of the locking member defines a sloped surface that is configured to engage a corresponding sloped surface of the pusher upon translation of the pusher relative to the cartridge assembly to translate the locking member relative to the sleeve member.

In one aspect, the sleeve member includes a flanged portion at a proximal end.

In one aspect, a distal end of the locking member includes a flanged portion that is configured to engage the flanged portion of the sleeve member upon translation of the locking member relative to the sleeve member.

In one aspect, a distal end of the sleeve member includes a lip that is configured to engage a recess in the head of the anvil assembly to removably secure the sleeve member to the anvil assembly.

In one aspect, a proximal end of the sleeve member includes a nub extending radially inward therefrom that is configured to engage a recess of the shaft.

A method of use for a surgical stapling device having an anvil assembly with a pivoting head is provided, the method including the steps of inserting the surgical stapling device into an opening in a body, positioning the surgical stapling device within the body such that a portion of tissue is disposed between an anvil assembly and a cartridge assembly of the surgical stapling device, translating the anvil assembly from a first position, where the anvil assembly is spaced from the cartridge assembly, to a second position where the anvil assembly approximated relative to the cartridge assembly to clamp the tissue therebetween, translating a staple pusher relative to the cartridge assembly to urge a plurality of fasteners disposed in the cartridge assembly through the tissue towards the anvil assembly, translating a locking member of the cartridge assembly relative to a sleeve member of the anvil assembly, the locking member engaging the sleeve member to axially maintain the sleeve member relative to the cartridge assembly, translating the anvil assembly from the second position to the first position, the sleeve member of the anvil assembly remaining engaged with the locking member after the anvil assembly has translated to the first position, the sleeve member disengaging from the anvil assembly to allow the head to pivot, pivoting the head of the anvil assembly and withdrawing the surgical stapling device from the body.

In one aspect, the step of translating the staple pusher to urge a plurality of fasteners is performed during actuation of a first stroke of the surgical stapling device and the step of translating a locking member of the cartridge assembly is performed during actuation of a second separate stroke of the surgical stapling device.

In one aspect, during the second stroke, after the first stroke, a knife pusher of the cartridge assembly is engaged with a knife carrier of the cartridge assembly to translate the knife carrier relative to the cartridge assembly. The knife carrier engages the locking member to translate the locking member relative to the sleeve member.

In one aspect, during the first stroke, the knife pusher is disengaged from the knife carrier.

In one aspect, the step of translating the locking member includes the step of translating the staple pusher. During translation of the staple pusher, a sloped surface of the staple pusher engages with a corresponding sloped surface of the locking member to translate the locking member relative to the sliding sleeve.

In one aspect, the locking member includes a flanged portion and the step of translating the locking member includes the step of engaging the flanged portion of the locking member with a corresponding flanged portion of the sleeve member to axially maintain the sleeve member relative to the cartridge assembly.

In one aspect, the method further includes the step of translating a knife blade relative to the cartridge assembly to sever a portion of the tissue coaxially disposed about the sliding sleeve and radially between the sliding sleeve and a tissue contacting surface of the cartridge assembly. The portion of tissue remains coaxially disposed about the sliding sleeve and axially maintained relative to the cartridge assembly when the anvil assembly is translated from the second position to the first position.

A method of firing a surgical stapling device is provided, the method comprising the steps of positioning the surgical stapling device within a body such that a portion of tissue is disposed between an anvil assembly and a cartridge assembly of the circular surgical stapling device with the anvil assembly approximated relative to the cartridge assembly to clamp the portion of tissue therebetween, actuating a handle assembly of the surgical stapling device to perform a first, staple forming, stroke, and actuating the handle assembly of the surgical stapling device to perform a separate second, tissue severing, stroke after the first, staple forming, stroke.

In one aspect, the first stroke includes translating a staple pusher of the cartridge assembly distally to urge a plurality of fasteners disposed in the cartridge assembly through the tissue towards the anvil assembly.

In one aspect, during a return portion of the first stroke, after staple forming, a knife pusher of the cartridge assembly is translated proximally to engage a knife assembly of the cartridge assembly.

In one aspect, the return portion of the first stroke includes translating the staple pusher proximally such that a flange of the staple pusher engages the knife pusher to translate the knife pusher proximally.

In one aspect, the second stroke includes translating the knife pusher distally to drive the knife assembly distally to sever tissue.

In one aspect, the knife pusher is disengaged from the knife assembly prior to the first stroke.

Any of the above aspects of the present disclosure described may be combined with any other aspect of the present disclosure without departing from the scope of the present disclosure.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIG. 14A is a side, cross-sectional view of the anvil assembly and cartridge assembly of FIG. 13A, illustrating the second stroke;

FIG. 14B is a perspective, cross-sectional view of the anvil assembly and cartridge assembly of FIG. 14A;

FIG. 18A is a perspective view of the anastomosis after the circular stapler has been removed;

FIG. 18B is a perspective, cross-sectional view of the anastomosis of FIG. 18A;

DETAILED DESCRIPTION OF EMBODIMENTS

Embodiments of the presently disclosed circular stapling instrument including independently actuated staple forming and cutting strokes and a tilt-able anvil head will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
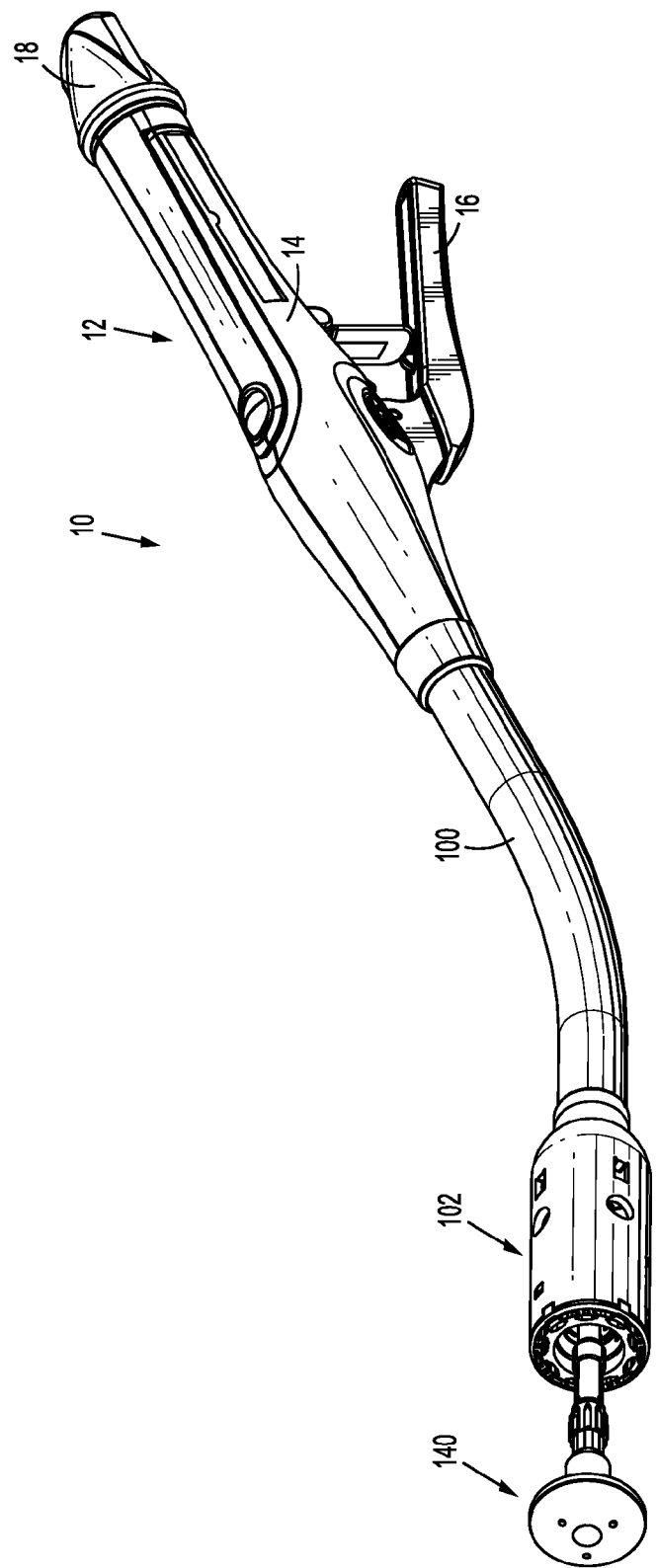
FIG. 1 is a perspective view of an exemplary circular stapler according to the present disclosure.
Figure 3:
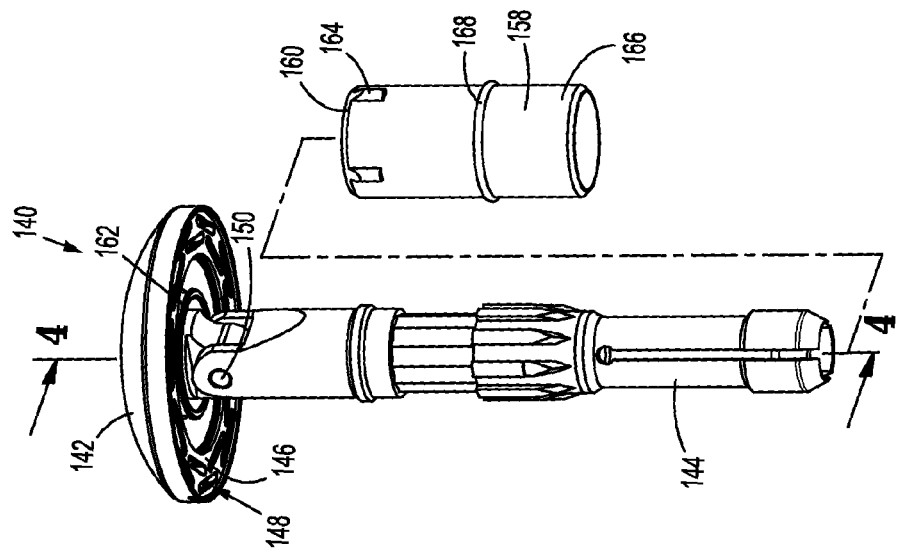
FIG. 3 is an exploded perspective view of the anvil assembly of FIG. 2.
Figure 2:
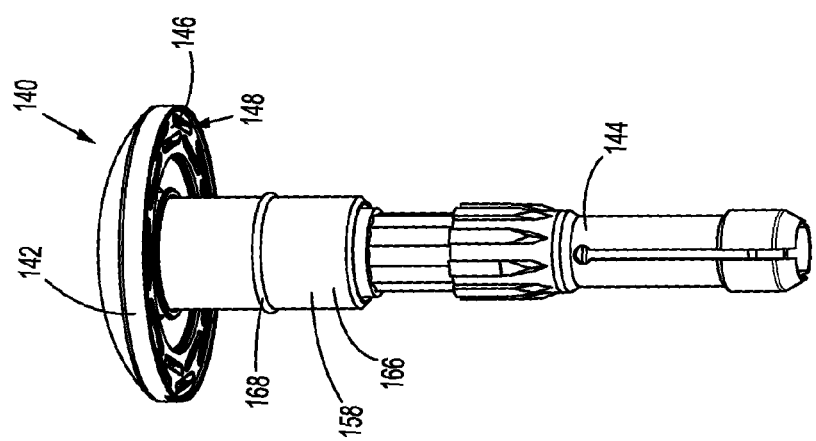
FIG. 2 is a perspective view of an anvil assembly of the circular stapler of FIG. 1.
Figure 4:
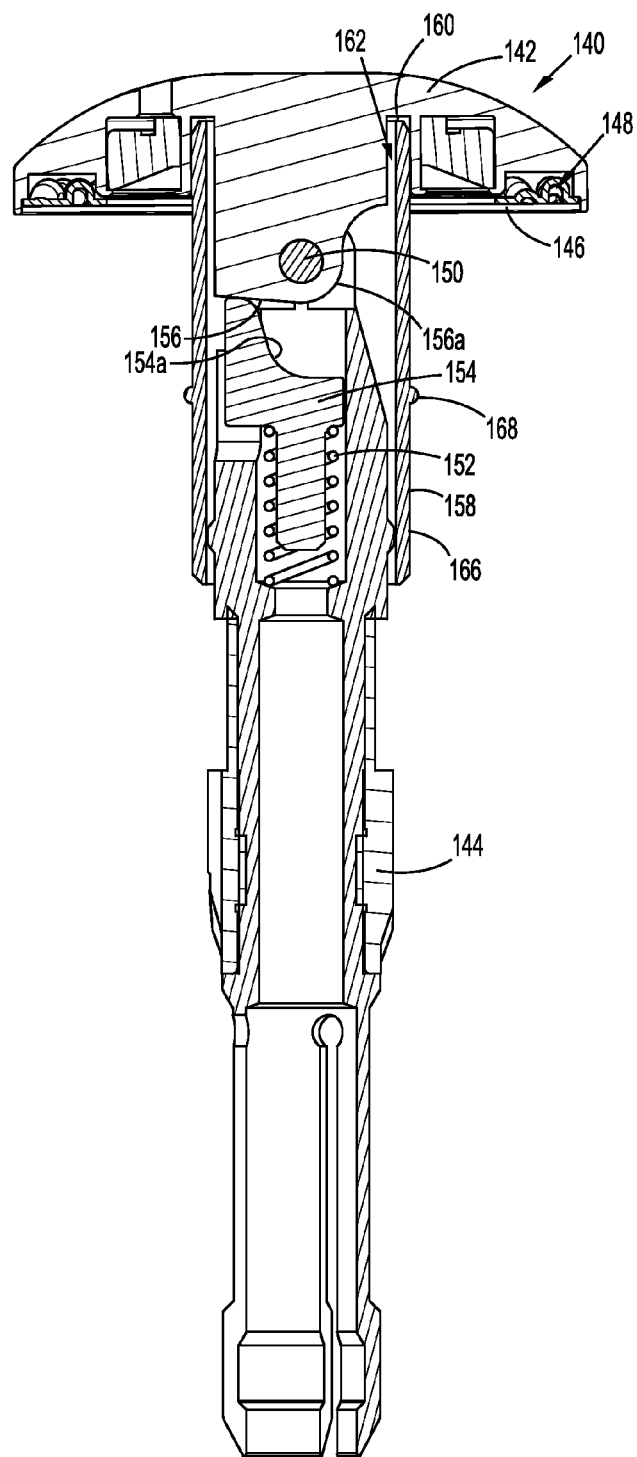
FIG. 4 is a side, cross-sectional view of the anvil assembly of FIG. 2.

Referring initially to FIG. 1, a circular stapler is disclosed herein and is generally designated as circular stapler 10. Circular stapler 10 includes a handle assembly 12 and an elongate body 100 coupled to a distal end of handle assembly 12. A cartridge assembly 102 is mounted on a distal end of elongate body 100.

Handle assembly 12 includes a fixed handle 14 and a moveable handle or trigger 16. Handle assembly 12 also includes an adjustment knob 18 for moving anvil assembly 140 relative to cartridge assembly 102. The structure and function of handle assembly 12 will only be described herein to the extent necessary to fully disclose the operation of cartridge assembly 102. Examples of instruments for performing circular anastomosis of hollow organs are described in U.S. Pat. Nos. 6,053,390, 5,588,579, 5,119,987, 5,005,749, 4,646,745, 4,576,167, and 4,473,077, each of which is incorporated herein in its entirety by reference. For example, the instrument may include a threaded or grooved shaft arranged to retract the anvil assembly of the circular instrument. A similar threaded or grooved shaft can be used to advance a drive member for advancing a series of pushers, for advancing a knife or knife holder, or both. It is envisioned that cartridge assembly 102 may be modified for use with any actuation assembly capable of advancing a drive member for a first function, and retracting and re-advancing the drive member for a second function. Alternatively, the actuation mechanism may have a first drive member for performing a first function and a second drive member for performing a second function or a single drive member may perform both the first and second functions at the same time. It is envisioned that the anvil assembly and cartridge assembly can be configured as a tool assembly that is a removable and replaceable unit that can connect with a motorized handle assembly, robotic surgical system, a pneumatic handle assembly, or other surgical handle assembly.

Elongate body 100 may extend from handle assembly 12 or may be removably attached to handle assembly 12 and may be constructed so as to have a curved shape along its length, and/or may be flexible or rigid.

Handle assembly 12 may include a powered actuation mechanism configured to supply linear motion through elongate body 100 to cartridge assembly 102. For example, handle assembly 12 may include an electric motor or other electrical device (not shown) which produces rotational motion upon actuation trigger 16 and converts the rotational motion into linear motion which is transmitted through elongate body 100 via a drive assembly (not shown) for use by cartridge assembly 102. It is contemplated that the motor or other electrical device may instead produce linear motion directly. Examples of instruments including powered actuation mechanisms for use with surgical stapling devices are described in co-pending U.S. patent application Ser. No. 12/946,082 entitled "ADAPTERS FOR USE BETWEEN SURGICAL HANDLE ASSEMBLY AND SURGICAL END EFFECTOR" and co-pending U.S. patent application Ser. No. 13/331,047 entitled "HAND HELD SURGICAL HANDLE ASSEMBLY, SURGICAL ADAPTERS FOR USE BETWEEN SURGICAL HANDLE ASSEMBLY AND SURGICAL END EFFECTORS, AND METHODS OF USE", each of which is incorporated herein in its entirety by reference.

Cartridge assembly 102 defines a longitudinal axis A-A. In one embodiment, cartridge assembly 102 is removably secured to elongate body 100 such that cartridge assembly 102 may be replaced and the circular stapler 10 may be reused. Alternatively, circular stapler 10 is configured for a single use, i.e., disposable.

Circular stapler 10 (FIG. 1) also includes an anvil assembly 140 positioned distally of cartridge assembly 102 and removably insertable into cartridge assembly 102. Anvil assembly 140 is translatable along longitudinal axis A-A relative to cartridge assembly 102.

Figure 10A:
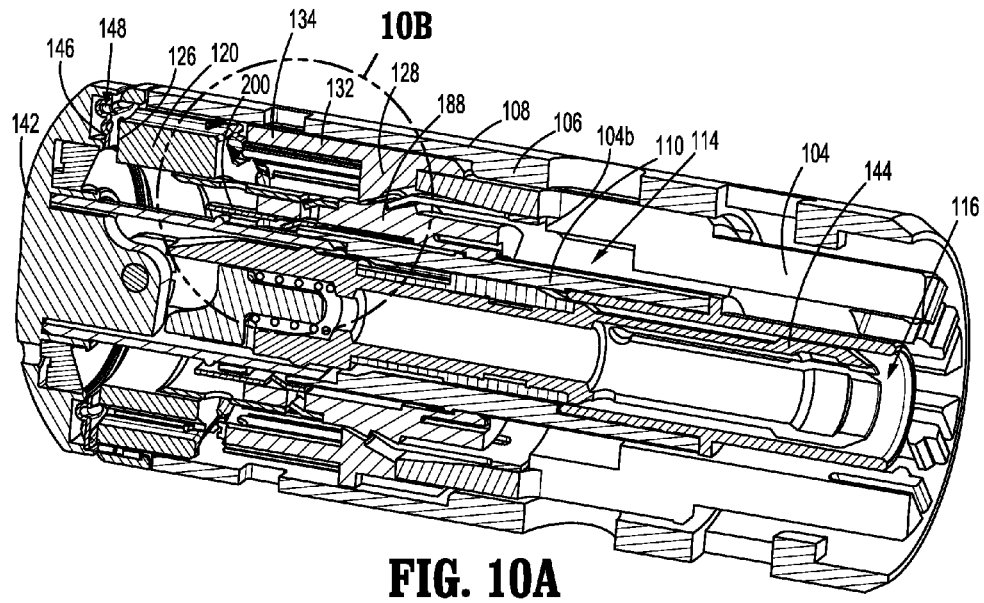
FIG. 10A is a perspective, cross-sectional view of the anvil assembly and cartridge assembly of the circular stapler of FIG. 1, illustrating the anvil assembly approximated relative to the cartridge assembly.

With reference now to FIGS. 2-5, anvil assembly 140 includes an anvil head 142 and an anvil shaft 144. Anvil shaft 144 is insertable into an inner bore 116 (FIG. 10A) of cartridge assembly 102 and is removably and slidably securable within inner bore 116 of cartridge assembly 102. Shaft 144 is configured to be actuatable by handle assembly 12 (FIG. 1) to translate anvil assembly 140 axially along longitudinal axis A-A relative to cartridge assembly 102 to approximate or un-approximate anvil assembly 140 relative to cartridge assembly 102. For example, adjustment knob 18 (FIG. 1) may be actuated to translate anvil assembly 140 relative to cartridge assembly 102.

Anvil head 142 includes a tissue contacting surface 146 defining staple forming pockets 148. In an initial condition (FIG. 4), tissue contacting surface 146 is configured to be substantially perpendicular to longitudinal axis A-A, with the tissue contacting surface 146 facing a tissue contacting surface of the staple cartridge. Anvil head 142 is coupled to anvil shaft 144 by a joint or pivot 150 and is rotatable about joint 150 to tilt anvil head 142 to a final tilted condition (FIGS. 16 and 17) such that tissue contacting surface 146 is transverse to the staple cartridge tissue contacting surface and may be substantially parallel to longitudinal axis A-A. Anvil head 140 is spring biased toward the final tilted condition by a spring 152 and a plunger 154 disposed in anvil shaft 144. Plunger 154 is configured to engage a proximal surface 156 of anvil head 142 adjacent or proximate to joint 150 and to urge anvil head 142 toward the final tilted condition due to the bias of spring 152. The anvil head has a proximal surface 156 and plunger 154 is also dimensioned to securely engage proximal surface 156 of anvil head 142 when anvil head 142 is in the final tilted condition. For example, plunger 154 may include an annular surface 154a which is configured to engage a corresponding annular surface 156a of anvil head 142 to secure anvil head 142 in the final tilted condition.

Anvil assembly 140 also includes a sliding sleeve 158 coaxially mounted about anvil shaft 144 and axially translatable along longitudinal axis A-A. The distal end 160 of sliding sleeve 158 is configured to engage a recess 162 in anvil head 142 to prevent anvil head 142 from transitioning from the initial un-tilted condition to the final tilted condition. The anvil head 142 has a recess 162 for receiving the sliding sleeve 158. Distal end 160 of sliding sleeve 158 includes raised surfaces 164 (FIG. 5) which create a friction or interference fit with recesses 162 of anvil head 142 to removably secure distal end 160 of sliding sleeve 158 within recesses 162 of anvil head 142. A proximal portion 166 of sliding sleeve 158 includes a nub or protrusion 168 for engagement with a locking sleeve 200 of cartridge assembly 102 as will be described in more detail below.

With reference now to FIGS. 5-10, cartridge assembly 102 includes a drive member 104, a housing 106, a staple cartridge 120, a staple pusher 128, a knife assembly 180, and a locking sleeve 200. Staple cartridge 120 is operably mounted at a distal end of cartridge assembly 102 and, in one embodiment, staple cartridge 120 is removably secured to cartridge assembly 102 such that staple cartridge 120 may be replaced.

With reference now to FIGS. 10A-10C and 11B, housing 106 of cartridge assembly 102 includes an outer cylindrical portion 108, an inner cylindrical portion 110 and a plurality of radially extending supports or ribs 112 extending between inner cylindrical portion 110 and outer cylindrical portion 108. Inner cylindrical portion 110 and outer cylindrical portion 108 of housing 106 are coaxial and define an annular channel 114 therebetween configured to receive a staple pusher 128 and knife assembly 180.

An inner bore 116 (FIGS. 10A and 11B) of cartridge assembly 102 extends through inner cylindrical portion 110 and is configured to receive shaft 144 of anvil assembly 140 therein for operable connection to adjustment knob 18 (FIG. 1) Inner bore 116 includes an enlarged portion 116a configured to receive a portion of sliding sleeve 158 therein when anvil assembly 140 is approximated relative to cartridge assembly 102.

Figure 10B:
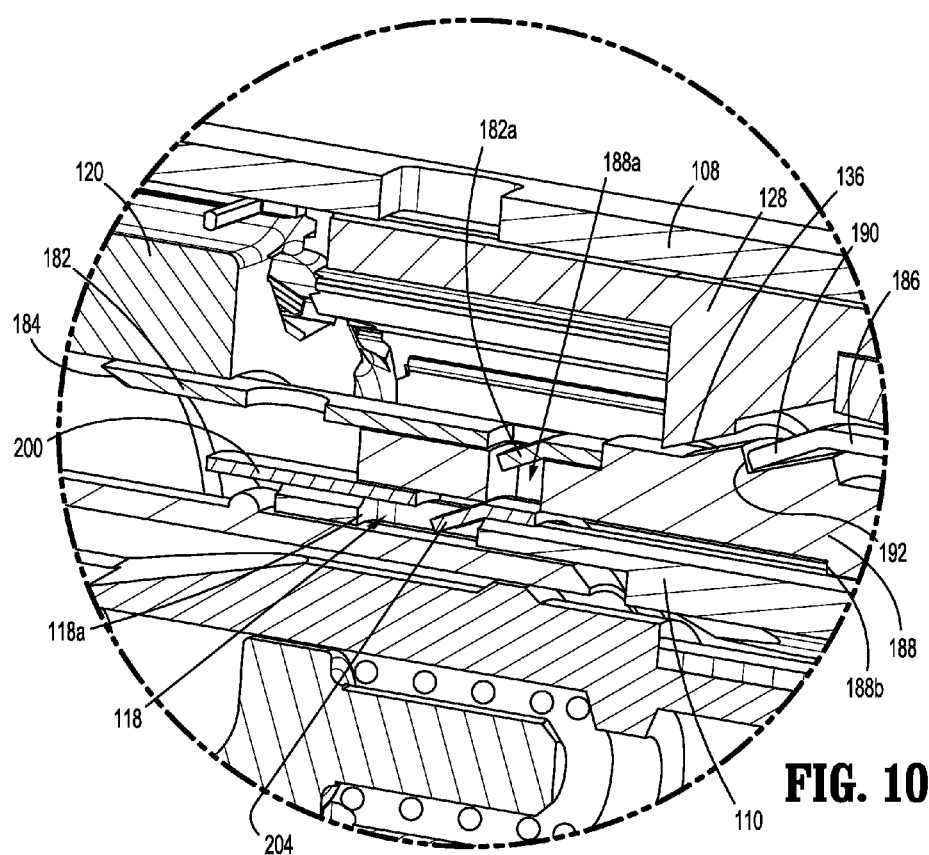
FIG. 10B is perspective, cross-sectional view of the area of detail depicted in FIG. 10A, illustrating the tab of the locking sleeve engaged with the slot of the inner cylindrical portion.
Figure 10C:
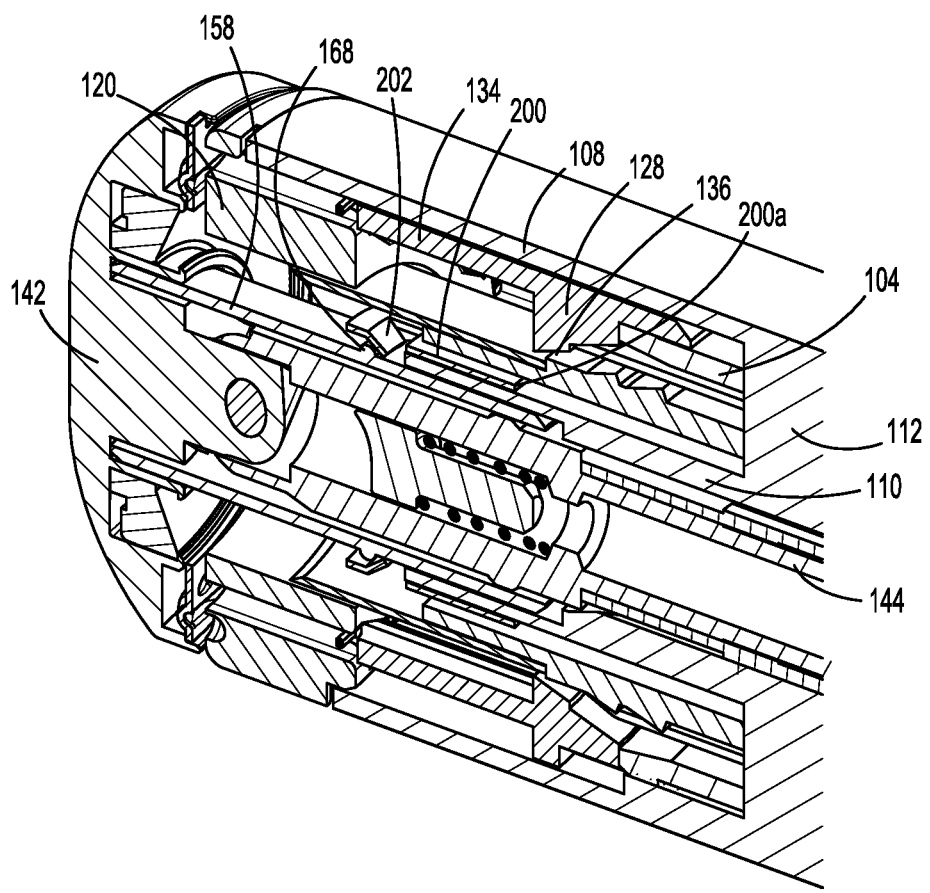
FIG. 10C is a perspective, cross-sectional view of the anvil assembly and cartridge assembly of FIG. 1, illustrating the relative positions of the flange portion of the locking sleeve and the nub of the sliding sleeve.

As illustrated in FIG. 10B, inner cylindrical portion 110 of housing 106 further includes a longitudinally extending slot 118 extending along an outer surface thereof and configured to slidably receive a tab 204 (FIGS. 5 and 6) of locking sleeve 200. Slot 118 and tab 204 allow locking sleeve 200 to slide longitudinally relative to inner cylindrical portion 110. Slot 118 defines a distal end 118a configured to engage tab 204 such that slot 118 maintains locking sleeve 200 within cartridge assembly 102 when locking sleeve 200 is in a distal most position with tab 204 of locking sleeve 200 engaged against distal end 118a of slot 118 of inner cylindrical portion 110.

Figure 5:
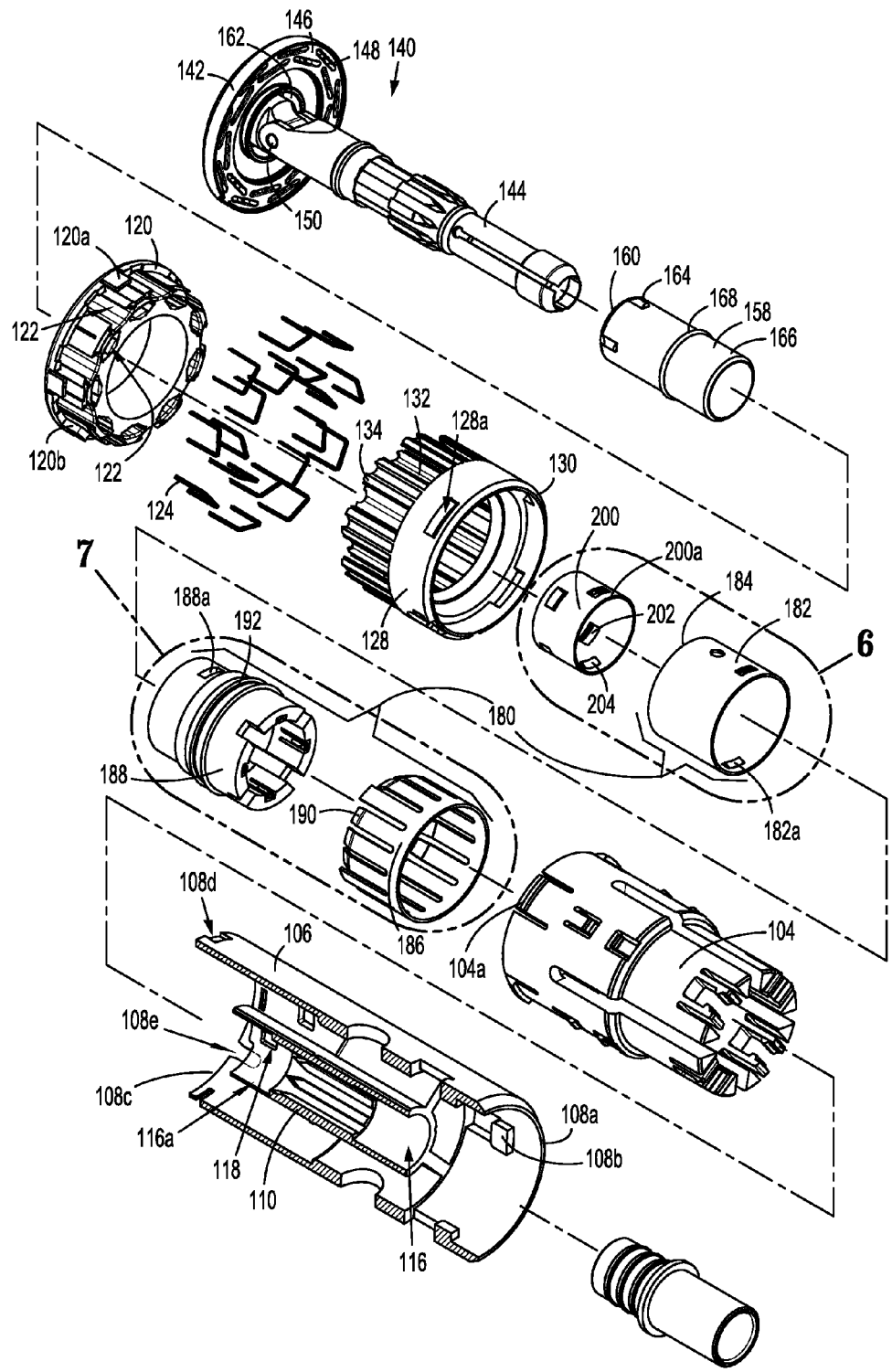
FIG. 5 is an exploded perspective view of the anvil assembly and a cartridge assembly of the circular stapler of FIG. 1.

With reference now to FIG. 5, a proximal end 108a of outer cylindrical portion 108 of housing 106 includes a tab 108b (FIG. 5) configured to operably couple cartridge assembly 102 to a distal end of elongate body 100. The elongate body 100 has an outer cylindrical portion 108 with a distal end 108c. A distal end 108c of outer cylindrical portion 108 defines a plurality of recesses 108d formed thereabout and configured to receive mounting tabs 120a of staple cartridge 120. Distal end 108c of outer cylindrical portion 108 also defines a slot 108e configured to receive a projection 120b formed on staple cartridge 120. Slot 108e is positioned such that when projection 120b is received in slot 108e, mounting tabs 120a of staple cartridge 120 are properly aligned with recesses 108d.

With reference now to FIGS. 5, 8A-8B and 17, staple cartridge 120 includes at least one annular array of staple receiving slots 122 disposed at a distal end and a staple 124 disposed in each of staple receiving slots 122. For example, staple cartridge 120 may include one, two, or more than two annular arrays of staple receiving slots 122. Staple receiving slots 122 extend through a tissue contacting surface 126 of the distal end of the staple cartridge 120. Staple cartridge 120 may be fixedly connected to the distal end of cartridge assembly 102 or may be configured to concentrically fit within the distal end of cartridge assembly 102.

With reference again to FIGS. 5 and 10A, staple pusher 128 defines a substantially cylindrical shape and has a proximal portion 130 and a distal portion 132. Staple pusher 128 is coaxially and slidably disposed within the channel 114, between outer cylindrical portion 108 and inner cylindrical portion 110. Distal portion 132 of staple pusher 128 defines a plurality of peripherally spaced fingers 134 in two concentric rows for engaging staples 124 within staple receiving slots 122. It is contemplated that one, two or more rows of fingers 134 may be included to correspond to the number of annular arrays of staple receiving slots 122 of staple cartridge 120. Each finger 134 of staple pusher 128 is received within one of the respective staple receiving slots 122 of staple cartridge 120 and is configured to translate through its respective staple receiving slot 122 during advancement of staple pusher 128 relative to cartridge assembly 102 to engage, drive and eject a respective staple 124 out of the staple receiving slot 122, through tissue, and against a staple forming pocket 148 of anvil assembly 140 to thereby form staple 124. For example, staples 124 may be formed in a substantially B-shape.

With reference to FIGS. 5, 8A-8B and 10A, drive member 104 is slidably received within channel 114 of cartridge assembly 102 and is axially translatable within cartridge assembly 102 in response to actuation of trigger 16 (FIG. 1) of handle assembly 12 (FIG. 1). Drive member 104 is operatively coupled to staple pusher 128 and configured to advance staple pusher 128 axially through cartridge assembly 102 and staple receiving slots 122 to urge staples 124 out of staple receiving slots 122. Drive member 104 includes a plurality of tabs 104a and staple pusher 128 includes corresponding recesses 128a for receiving tabs 104a to couple staple pusher 128 to drive member 104. Drive member 104 may be coupled to staple pusher 128 through other methods including, for example, snap fit, friction fit, or other similar methods of coupling. Drive member 104 and staple pusher 128 may alternatively be monolithically formed.

With reference now to FIGS. 5-10, cartridge assembly 102 includes a knife assembly 180 slidably disposed in channel 114, radially inward of staple cartridge 120 and coaxially disposed about inner cylindrical portion 110 of housing 106. Knife assembly 180 is axially translatable along longitudinal axis A-A to sever a portion of the tissue disposed radially inward of staple cartridge 120 during actuation of circular stapler 10. Knife assembly 180 includes a knife blade 182 substantially in the form of an open cup or cylinder with the distal end thereof defining a knife edge 184.

Figure 6:
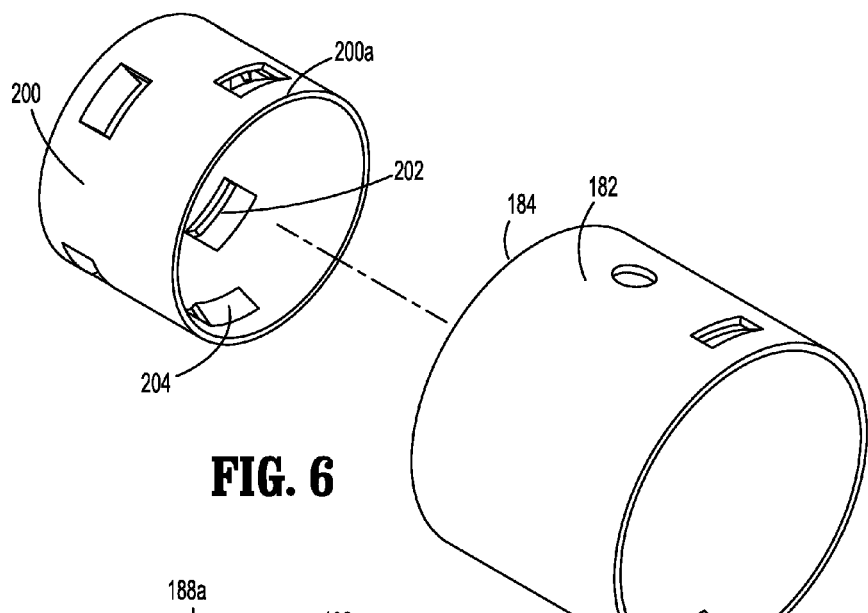
FIG. 6 is an enlarged perspective view of the locking sleeve and knife blade of FIG. 5.
Figure 7:
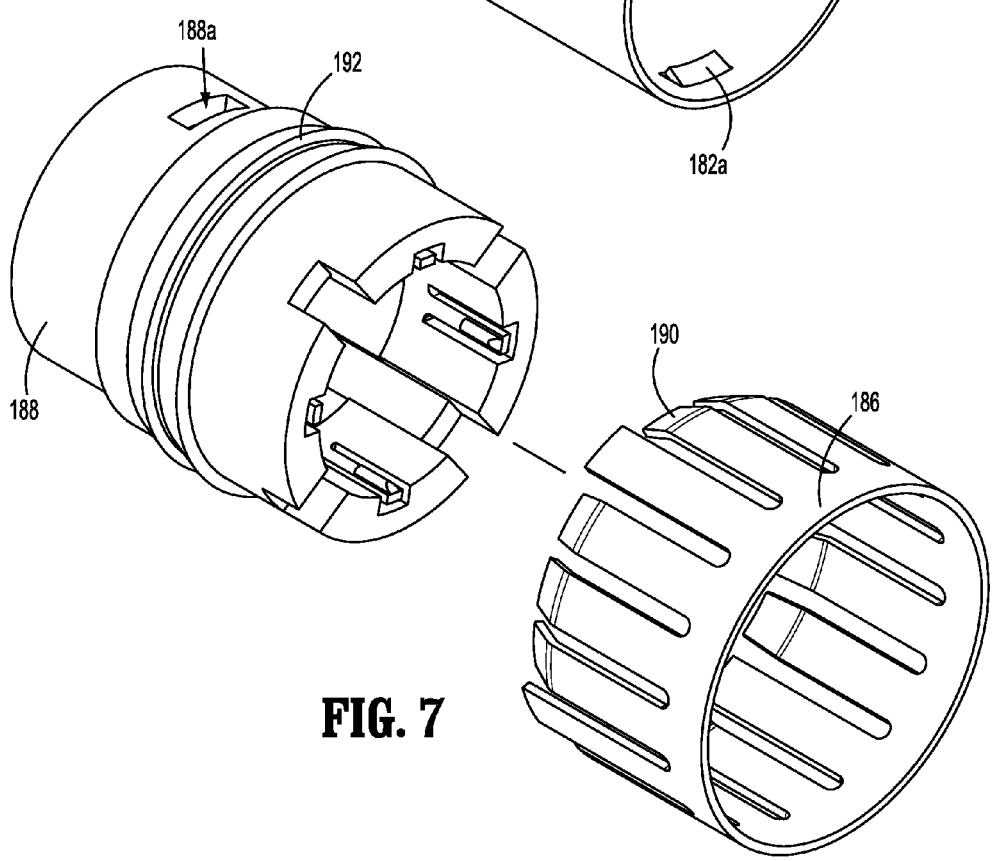
FIG. 7 is an enlarged perspective view of the knife carrier and knife pusher of FIG. 5.
Figure 8A:
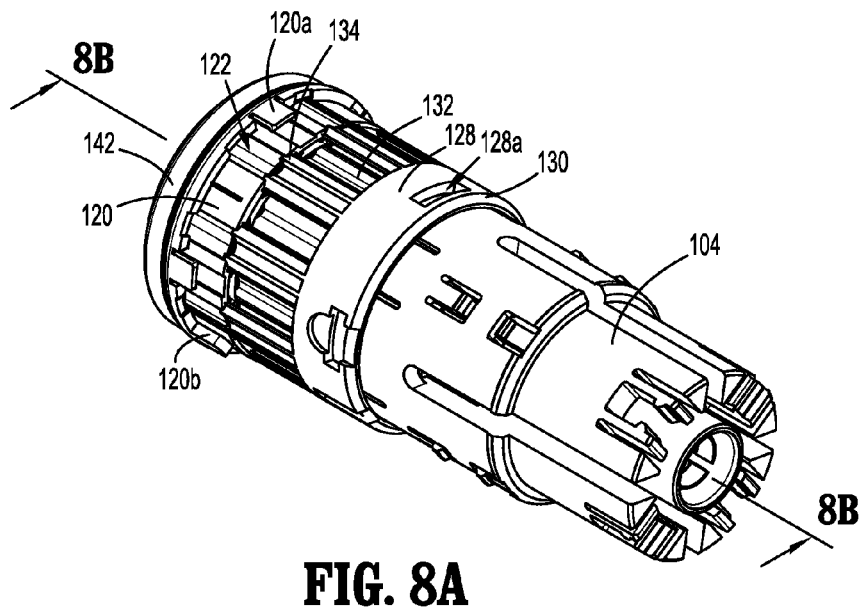
FIG. 8A is a perspective view of the anvil assembly and the cartridge assembly of the circular stapler of FIG. 1, illustrating the anvil assembly approximated relative to the cartridge assembly with the housing removed.
Figure 8B:
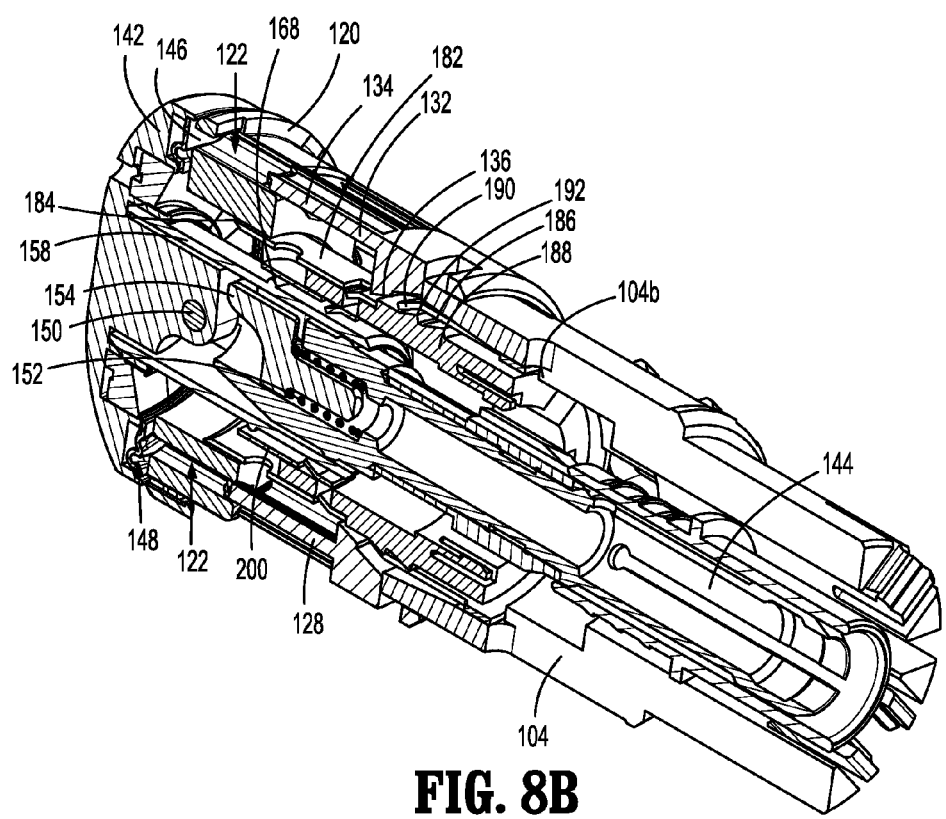
FIG. 8B is a perspective, longitudinal cross-sectional view of the anvil assembly and cartridge assembly of FIG. 8A, as taken through 8B-8B of FIG. 8A.
Figure 9A:
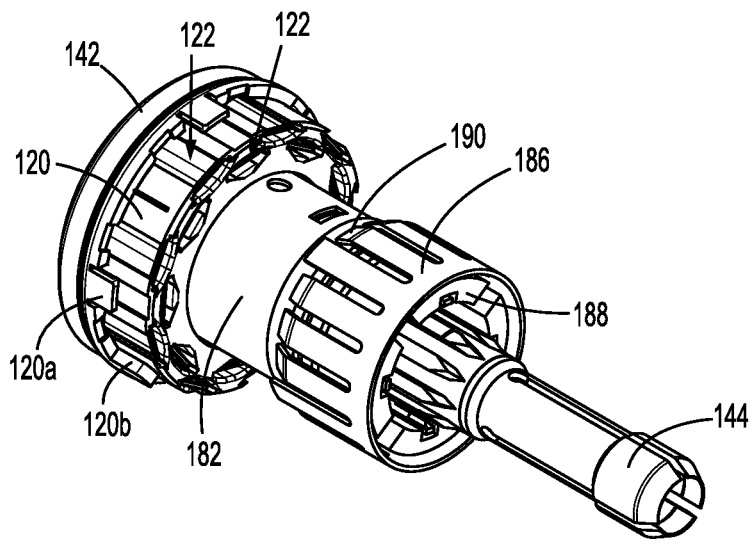
FIG. 9A is a perspective view of the anvil assembly and cartridge assembly of FIG. 8A, with the drive member and staple pusher removed.
Figure 9B:
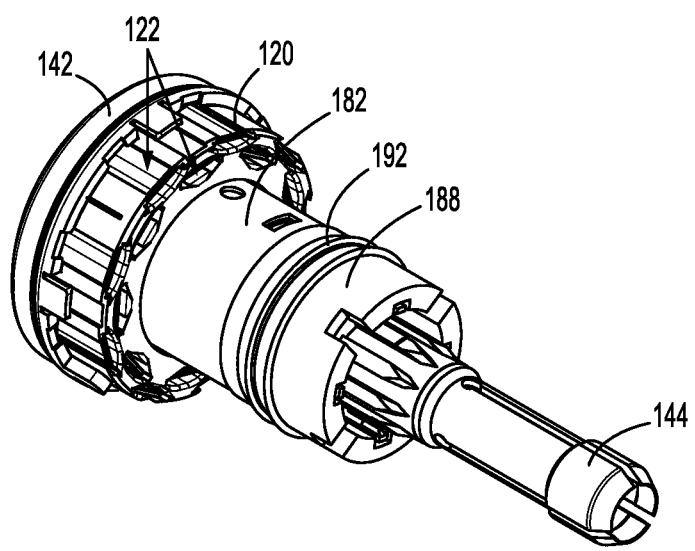
FIG. 9B is a perspective view of the anvil assembly and cartridge assembly of FIG. 9A, with the knife pusher removed.

As seen in FIGS. 6-10, knife assembly 180 includes a knife pusher 186 and a knife carrier 188. Knife pusher 186 is engageable by drive member 104 such that distal advancement of drive member 104 causes distal advancement of knife pusher 186 along longitudinal axis A-A. Knife pusher 186 includes a plurality of resilient fingers 190 at a distal end which are configured for engaging an outer lip 192 of knife carrier 188. Knife carrier 188 is coupled to knife blade 182 and is axially translatable to drive knife blade 182 distally to sever tissue. Knife carrier 188 may be coupled to knife blade 182 by a snap fit, friction fit, or other similar methods of coupling. For example, as seen in FIG. 6, knife blade 182 may include tabs 182a, and, as seen in FIG. 7, knife carrier 188 may include corresponding recesses 188a configured to engage tabs 182a to couple knife blade 182 and knife carrier 188 together. Knife carrier 188 and knife blade 182 may alternatively be monolithically formed.

Drive member 104 is configured to engage a proximal end of knife pusher 186 during distal translation of drive member 104 to drive knife pusher 186 distally. Drive member 104 may include an inner lip 104b (FIGS. 8B and 10A) on an inner surface for engaging proximal end of knife pusher 186. In accordance with an embodiment of the present disclosure, in an initial position, resilient fingers 190 of knife pusher 186 are positioned distal of outer lip 192 of knife carrier 188 and are not engaged with outer lip 192. In one embodiment, this allows knife pusher 186 to be driven axially by drive member 104 to a second, distal position during a first stroke or stapling forming stroke without causing knife carrier 188 to translate axially. This allows staples 124 to be fired independent of a movement of knife blade 182 to sever tissue. Other embodiments of the circular stapler are contemplated in which the knife blade and staple pusher or pushers are independently actuated but the anvil does not tilt with respect to the staple cartridge, or the anvil assembly has a different anvil tilting mechanism.

With reference now to FIGS. 11B, 12A-12B, 13A-13B and 14A-14B, staple pusher 128 includes a flange 136 extending inwardly therefrom which is configured to engage resilient fingers 190 of knife pusher 186 during proximal translation of staple pusher 122 after the first stroke or staple forming stroke. Flange 136 engages resilient fingers 190 to drive and return knife pusher 186 from the second, distal position to the initial position during proximal translation of drive member 104 and staple pusher 128. In addition, flange 136 is configured to drive knife pusher 186 proximal of the initial position such that fingers 190 snap into or engage outer lip 192 of knife carrier 188. Once engaged with outer lip 192 of knife carrier 188, resilient fingers 190 of knife pusher 186 are configured to drive knife carrier 188 and knife blade 182 distally upon distal translation of knife pusher 186, during the second stroke to thereby sever tissue. It is contemplated that resilient fingers 190 may alternatively be initially engaged with outer lip 192 such that knife carrier 188 is also translated distally during the first stroke. It is also contemplated that knife pusher 186 and knife carrier 188 may be monolithically formed.

With reference now to FIGS. 5, 6, and 10A-10C, cartridge assembly 102 includes a locking sleeve 200 coaxially disposed about inner cylindrical portion 110 of cartridge assembly 102, adjacent knife carrier 188. Locking sleeve 200 is axially translatable relative to longitudinal axis A-A of cartridge assembly 102, and tab 204 thereof is slidably engaged with longitudinally extending slot 118 of inner cylindrical portion 110. A proximal end 200a of locking sleeve 200 is configured for engagement with an inner lip 188b of knife carrier 188 such that during distal translation of knife carrier 188, locking sleeve 200 is also translated distally. For example, the proximal end 200a of locking sleeve 200 may be coaxially positionable within knife carrier 188 to engage inner lip 188b.

As illustrated in FIG. 6, locking sleeve 200 defines a substantially cylindrical shape and includes a flange portion or tab 202 extending inwardly therefrom. Flange portion or tab 202 is configured to snap over and engage nub or protrusion 168 (FIGS. 5, 10C and 11B) disposed on an outer surface of sliding sleeve 158 after distal translation of locking sleeve 200 (FIGS. 14A and 14B), to secure sliding sleeve 158 in place relative to cartridge assembly 102. Once locking sleeve 200 has secured sliding sleeve 158 in place, anvil assembly 140 may be translated distally (FIGS. 16 and 17), after the second stroke of circular stapler 10, without also translating sliding sleeve 158 distally, thereby removing distal end 160 of sliding sleeve 158 from recesses 162 of anvil head 142. Once distal end 160 of sliding sleeve 158 is removed from recesses 162 of anvil head 142, anvil head 142 is free to tilt from the initial un-tilted condition to the final tilted condition due to the bias of spring 152 on plunger 154, as described above.

Figure 11A:
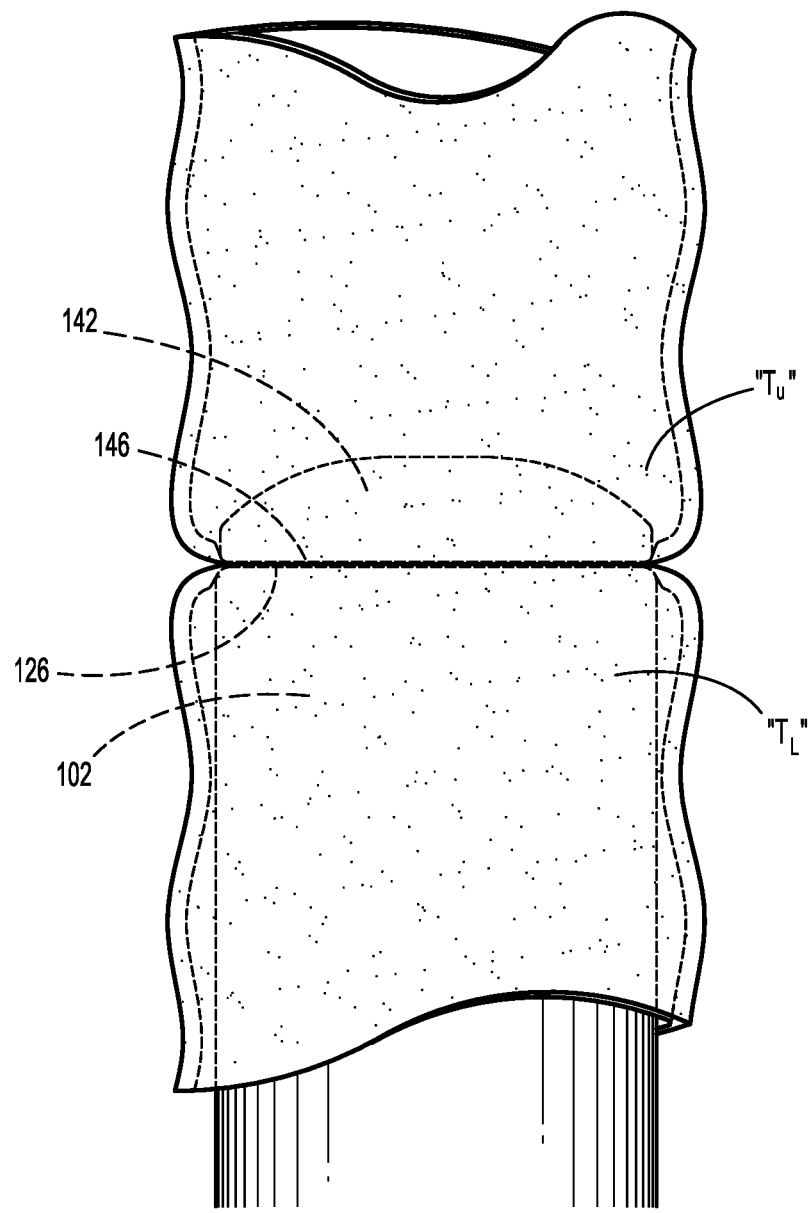
FIG. 11A is a side view of the anvil assembly and cartridge assembly of the circular stapler of FIG. 1, illustrating the anvil assembly approximated relative to the cartridge assembly to grasp tissue therebetween.
Figure 11B:
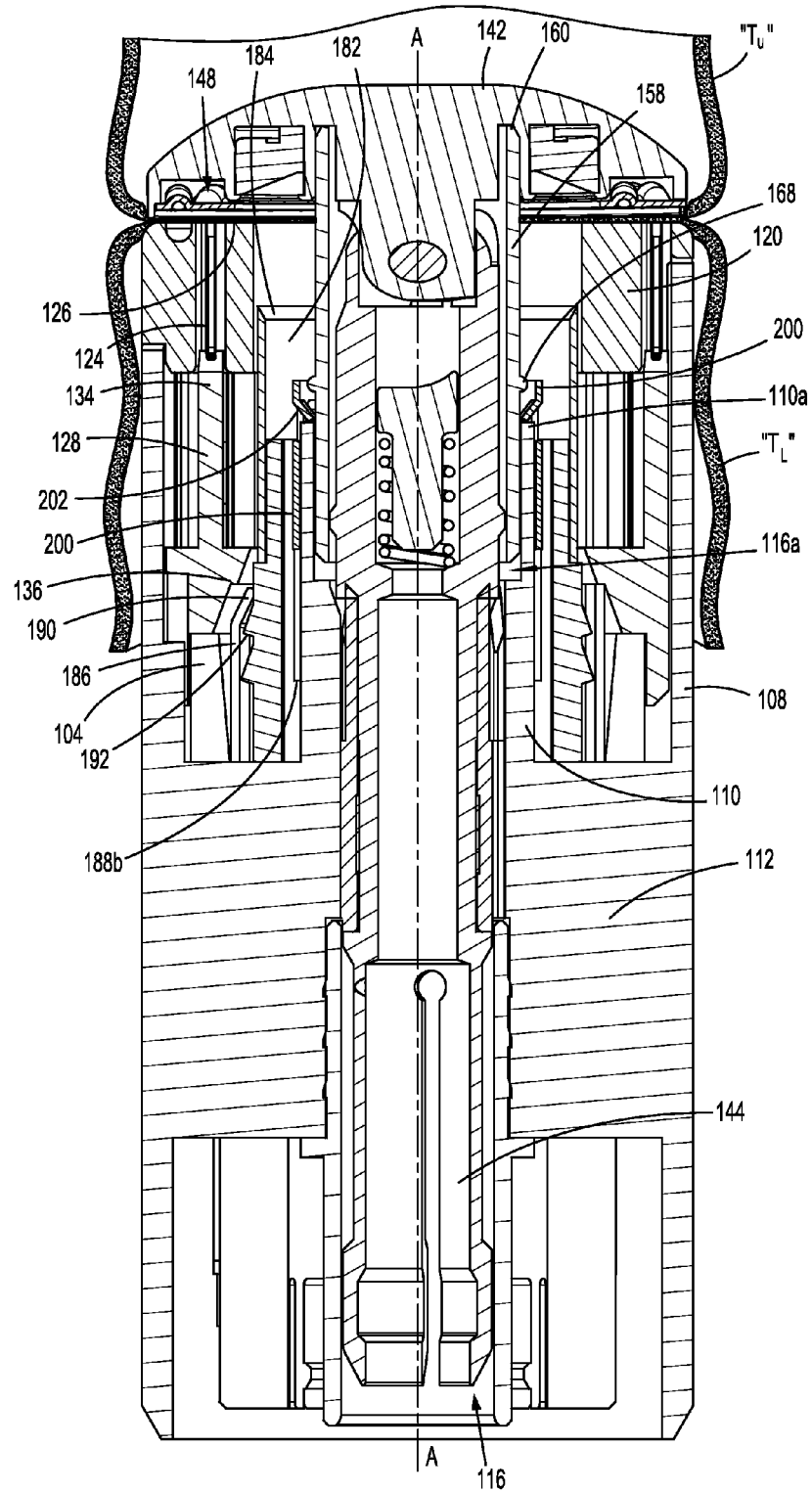
FIG. 11B is a side, cross-sectional view of the anvil assembly and cartridge assembly of FIG. 11A.

The operation of circular stapler 10 will now be described with reference to FIGS. 11A-18B. Referring initially to FIGS. 11A and 11B, cartridge assembly 102 is shown in an initial, or pre-fired condition, following approximation of anvil assembly 140 relative to cartridge assembly 102, with tissue "$T_U$ and $T_L$" to be anastomosed disposed therebetween. In the initial condition, drive member 104, staple pusher 128, knife pusher 186 and knife carrier 188 are disposed in initial proximal positions with resilient fingers 190 of knife pusher 186 disengaged from outer lip 192 of knife carrier 188 and positioned distal of outer lip 192.

Prior to firing, shaft 144 and sliding sleeve 158 of anvil assembly 140 are inserted through an upper portion of tissue "$T_U$", staple cartridge 120 is positioned against a lower portion of tissue "$T_L$" and shaft 144 is inserted through lower portion of tissue "$T_L$" into inner bore 116 of cartridge assembly 102. Anvil assembly 140 is then approximated relative to staple cartridge 120 to grasp the upper and lower portions of tissue "$T_U$ and $T_L$" disposed therebetween. When anvil assembly 140 and staple cartridge 120 are approximated, at least a portion of sliding sleeve 158 is positioned within inner bore 116 of housing 106, through the lower portion of tissue "$T_L$", with nubs 168 of sliding sleeve 158 disposed distal of a distal end 110a (FIG. 11B) of inner cylindrical portion 110. For clarity, upper and lower portions of tissue "$T_U$" and "$T_L$" will only be illustrated in the figures where necessary.

Figure 12B:
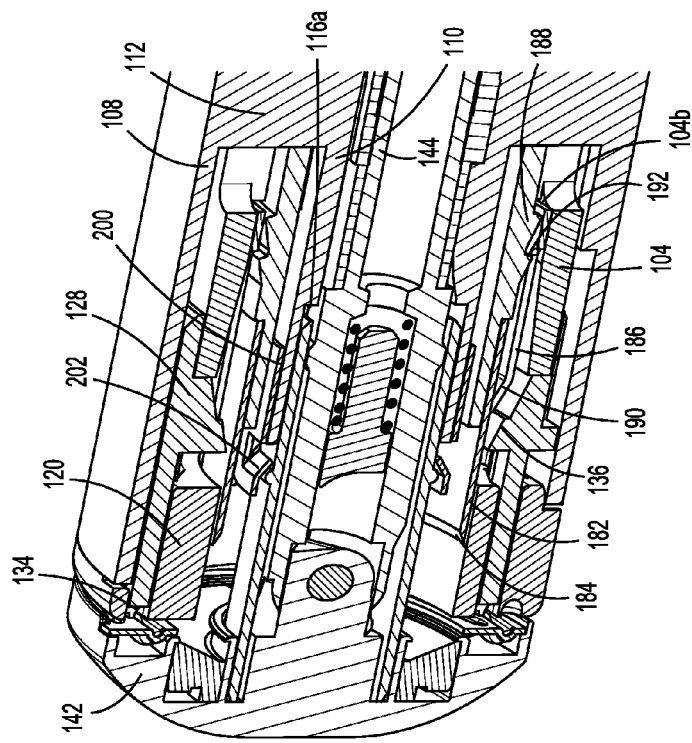
FIG. 12B is a perspective, cross-sectional view of the anvil assembly and cartridge assembly of FIG. 12A.
Figure 12A:
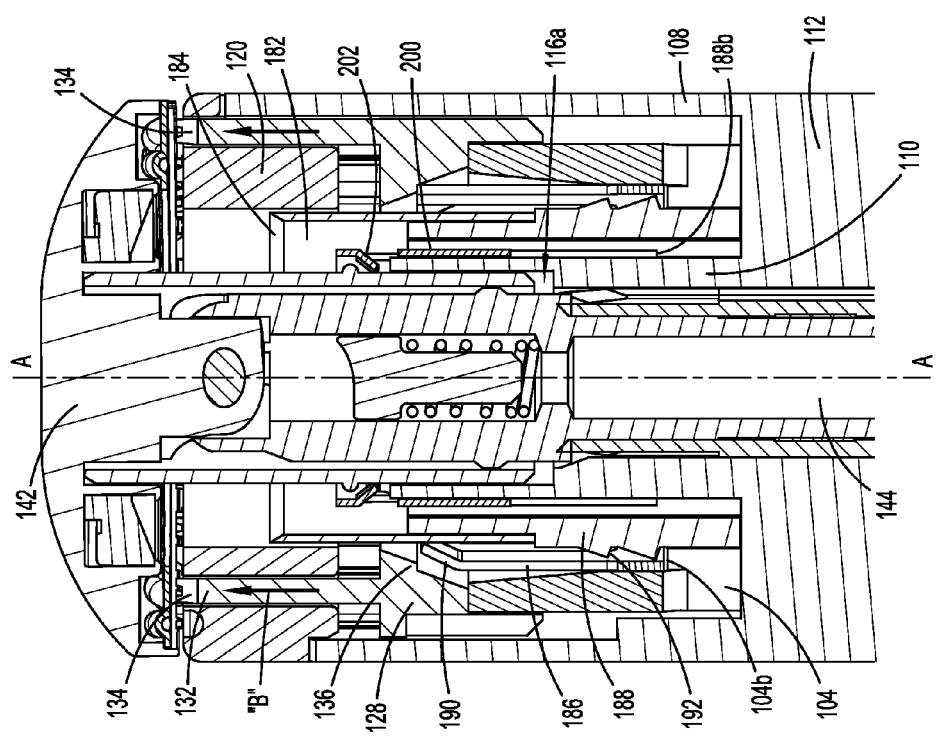
FIG. 12A is a side, cross-sectional view of the anvil assembly and cartridge assembly of FIG. 11B, illustrating the first stroke.

With reference now to FIGS. 12A and 12B, during the first stroke or staple forming stroke of circular stapler 10 (FIG. 1), following approximation of anvil assembly 140 against staple cartridge 120, retraction or actuation of trigger 16 (FIG. 1) relative to handle 14 (FIG. 1) causes advancement of a drive assembly (not shown) which operably engages drive member 104 to cause advancement of drive member 104 in the direction indicated by arrows "B" (FIG. 12A). As drive member 104 advances, drive member 104 engages and drives staple pusher 128 and knife pusher 186 in the direction indicated by arrows "B". It is important to note that during the first stroke, because resilient fingers 190 of knife pusher 186 are initially positioned distal of outer lip 192 of knife carrier 188, knife carrier 188 does not advance in the direction indicated by arrows "B" and thus knife blade 182 remains in the initial position.

As staple pusher 128 advances in the direction indicated by arrows "B", fingers 134 of staple pusher 128 advance through staple receiving slots 122 to drive or eject staples 124 out of staple receiving slots 122, through tissue portions "$T_U$" and "$T_L$" grasped between anvil assembly 140 and staple cartridge 120, and against staple forming pockets 148 of anvil assembly 140 to thereby form staples 124. Staples 124 secure upper and lower tissue portions "$T_U$" and "$T_L$" together to form an anastomosis (FIGS. 18A and 18B).

Figure 13B:
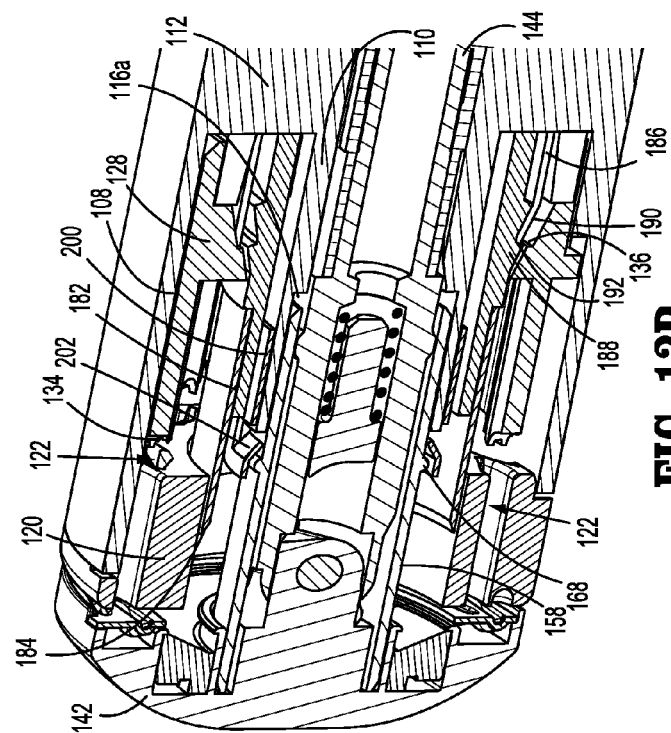
FIG. 13B is a perspective, cross-sectional view of the anvil assembly and cartridge assembly of FIG. 13A.
Figure 13A:
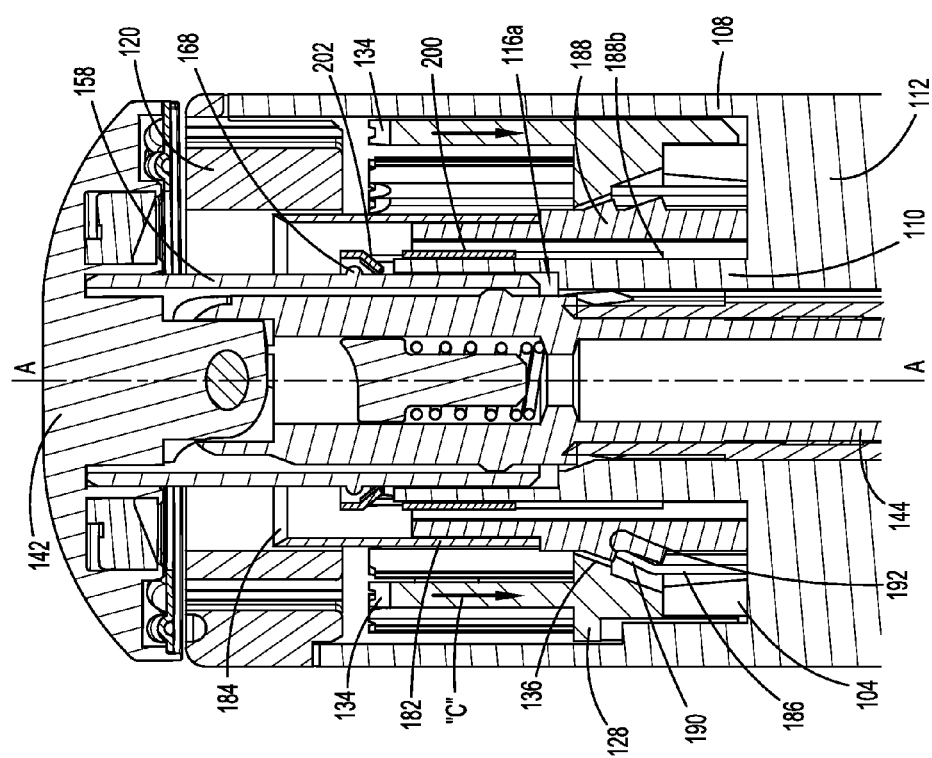
FIG. 13A is a side, cross-sectional view of the anvil assembly and cartridge assembly of FIG. 12A, illustrating the staple pusher and knife pusher moving to a proximal most position after the first stroke.

With reference now to FIGS. 13A and 13B, once staples 124 have been fired, drive member 104 is retracted in the direction indicated by arrows "C" during a return portion of the first stroke. As drive member 104 is retracted, staple pusher 128 is also retracted due to the coupling of tabs 104a and recesses 128a. As staple pusher 128 retracts in the direction indicated by arrows "C", flange 136 of staple pusher 128 engages resilient fingers 190 of knife pusher 186 to drive knife pusher 186 in the direction indicated by arrows "C". At the end of the return portion of the first stroke, drive member 104, staple pusher 128 and knife pusher 186 are sufficiently retracted to a position proximal of the initial position such that resilient fingers 190 of knife pusher 186 slot into or behind outer lip 192 of knife carrier 188.

Upon completion of the first or staple forming stroke and the return portion of the first stroke, in one embodiment, trigger 16 (FIG. 1) is released to permit the retraction of the drive member 104, staple pusher 128 and knife pusher 186. In other embodiments, the drive member 104, staple pusher 128 and knife pusher 186 may automatically retract upon completion of the first or staple forming stroke. As discussed above, knife pusher 186 is retracted to a position proximal of its initial position to allow resilient fingers 190 of knife pusher 186 to engage outer lip 192 of knife carrier 188.

Figure 16:
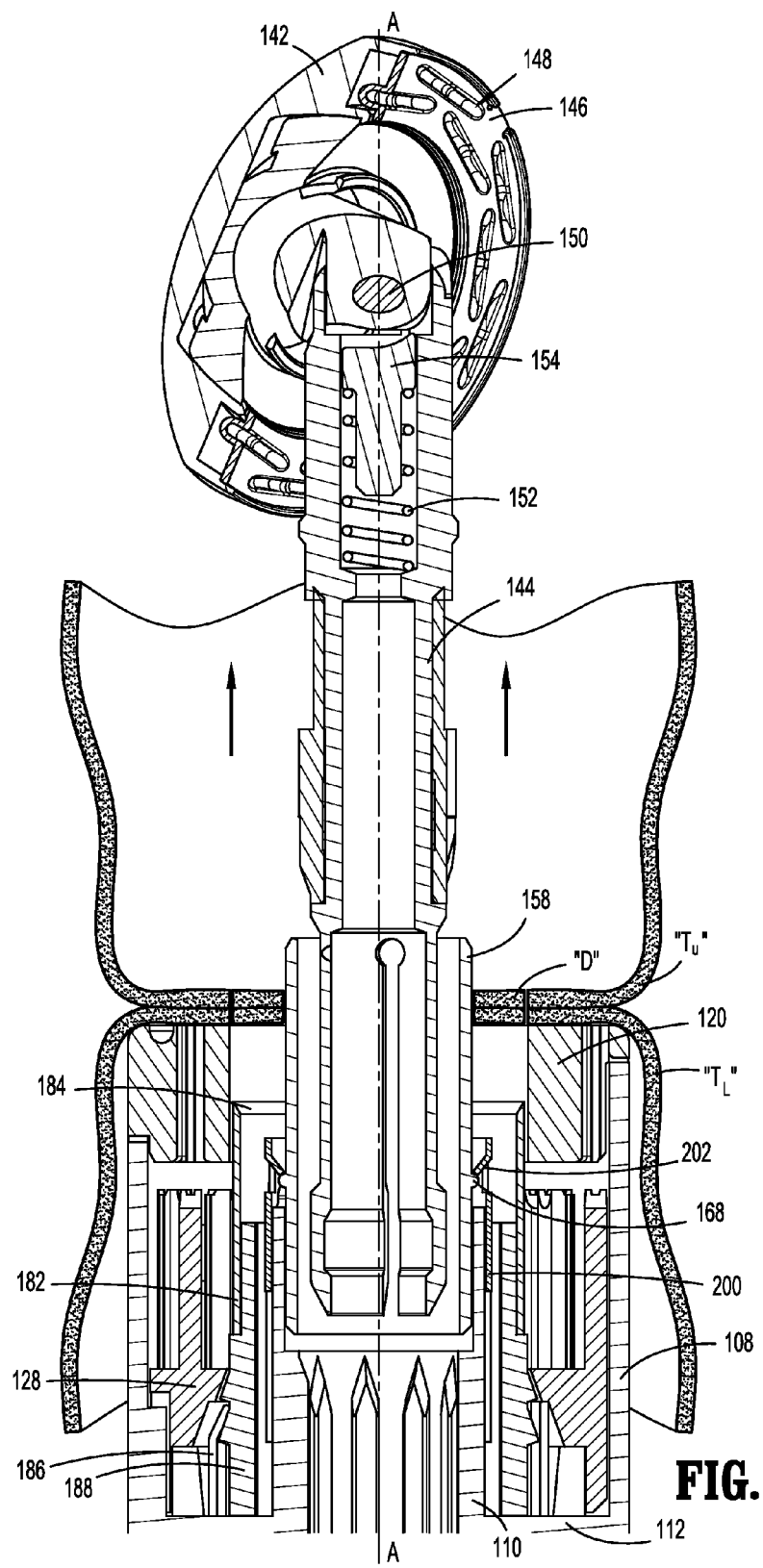
FIG. 16 is a side, cross-sectional view of the anvil assembly and cartridge assembly of FIG. 15, illustrating the anvil assembly un-approximated from the cartridge assembly after the second stroke with the sliding sleeve and anastomosis donut remaining in the cartridge assembly.
Figure 17:
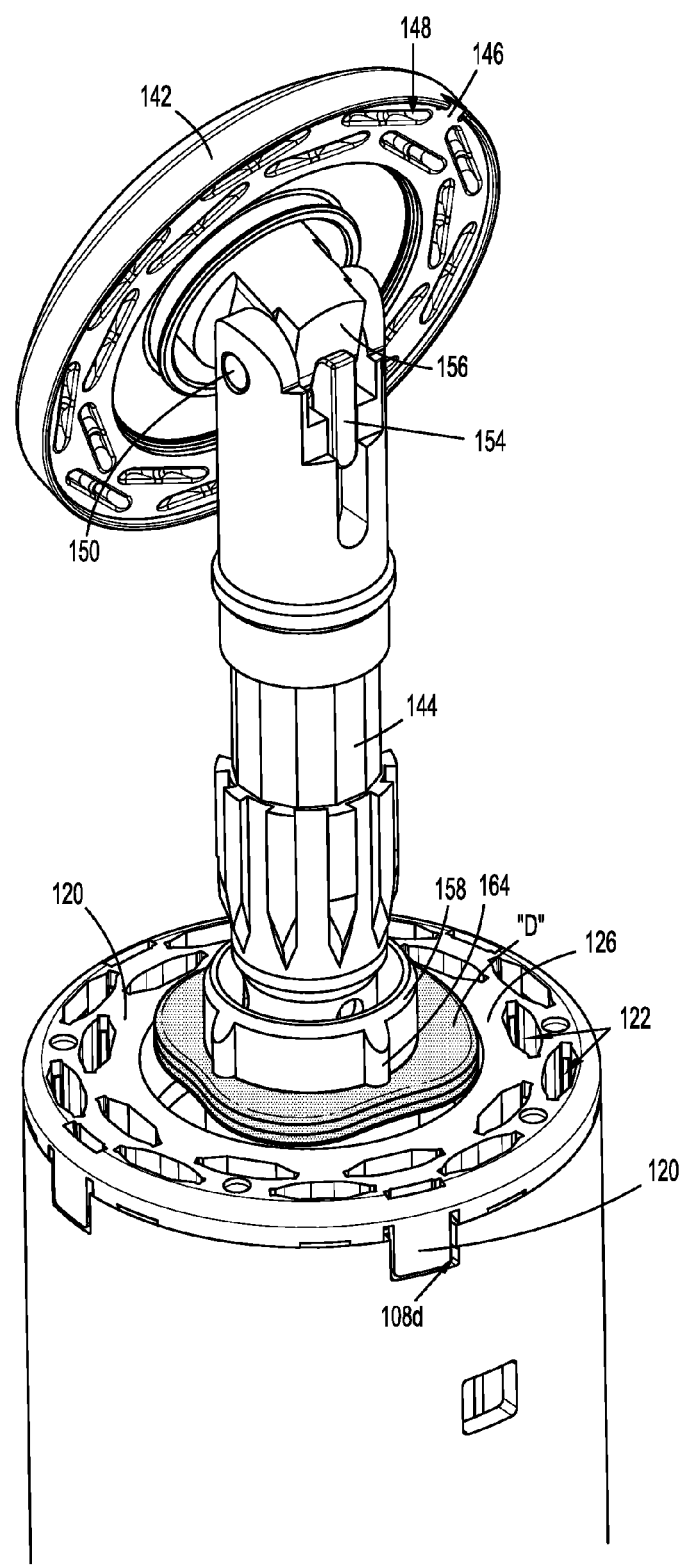
FIG. 17 is a perspective view of the anvil assembly and cartridge assembly of FIG. 16.
Figure 19:
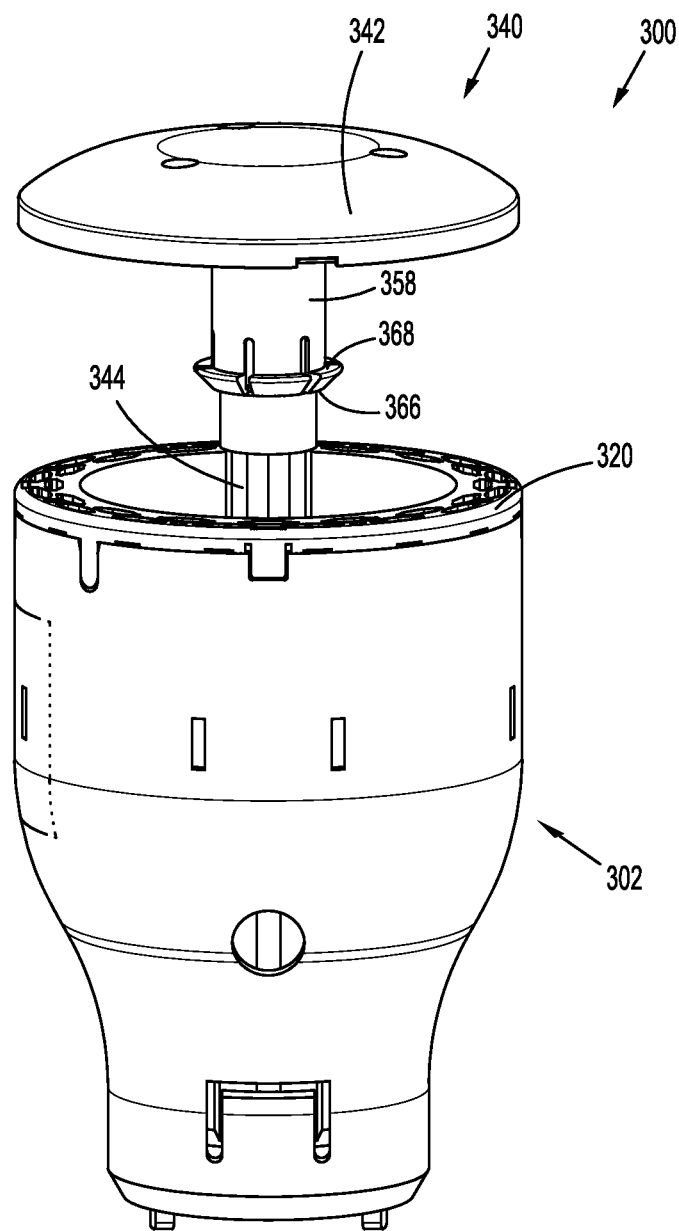
FIG. 19 is a perspective view of an alternate embodiment of circular stapler of FIG. 1.

With reference now to FIGS. 14A and 14B, during the second or cutting stroke of circular stapler 10 (FIG. 1), a second subsequent retraction or actuation of trigger 16 (FIG. 1) relative to handle 14 (FIG. 1) causes a re-advancement of the drive assembly (not shown) which operatively engages drive member 104 to cause advancement of pusher 128 and knife pusher 186 in the direction indicated by arrows "D". Since resilient fingers 190 of knife pusher 186 are now engaged with outer lip 192 of knife carrier 188, knife carrier 188 is also advanced by drive member 104 in the direction indicated by arrows "D". As knife carrier 188 advances in the direction indicated by arrows "D", knife blade 182 is also advanced due to the coupling of tabs 182a of knife blade 182 with recesses 188a of knife carrier 188. As knife blade 182 advances, knife edge 184 engages and severs the portion of upper and lower tissue portions "$T_U$" and "$T_L$" (FIGS. 16 and 17) disposed radially inward of staple cartridge 120, thereby forming an anastomosis donut "D" (FIGS. 16 and 17). The anastomosis donut "D" may be positioned coaxially about sliding sleeve 158 (FIGS. 16 and 17) of anvil assembly 140.

With reference again to FIGS. 14A and 14B, as knife carrier 188 is advanced in the direction indicated by arrows "D", inner lip 188b of knife carrier 188 engages proximal end 200a of locking sleeve 200 to thereby drive locking sleeve 200 in the direction indicated by arrows "D" until at least a portion of locking sleeve 200 is positioned coaxially about sliding sleeve 158 and flange portion 202 of locking sleeve 200 snaps over and engages nub or protrusion 168 of sliding sleeve 158. As locking sleeve 200 translates in the direction indicated by arrows "D", tab 204 of locking sleeve 200 slides along slot 118 of inner cylindrical portion 110. When flange portion 202 of locking sleeve 200 engages protrusions 168 of sliding sleeve, tab 204 may bottom out or abut distal end 118a of slot 118 or may be spaced from distal end 118a of slot 118 of inner cylindrical portion 110.

Figure 15:
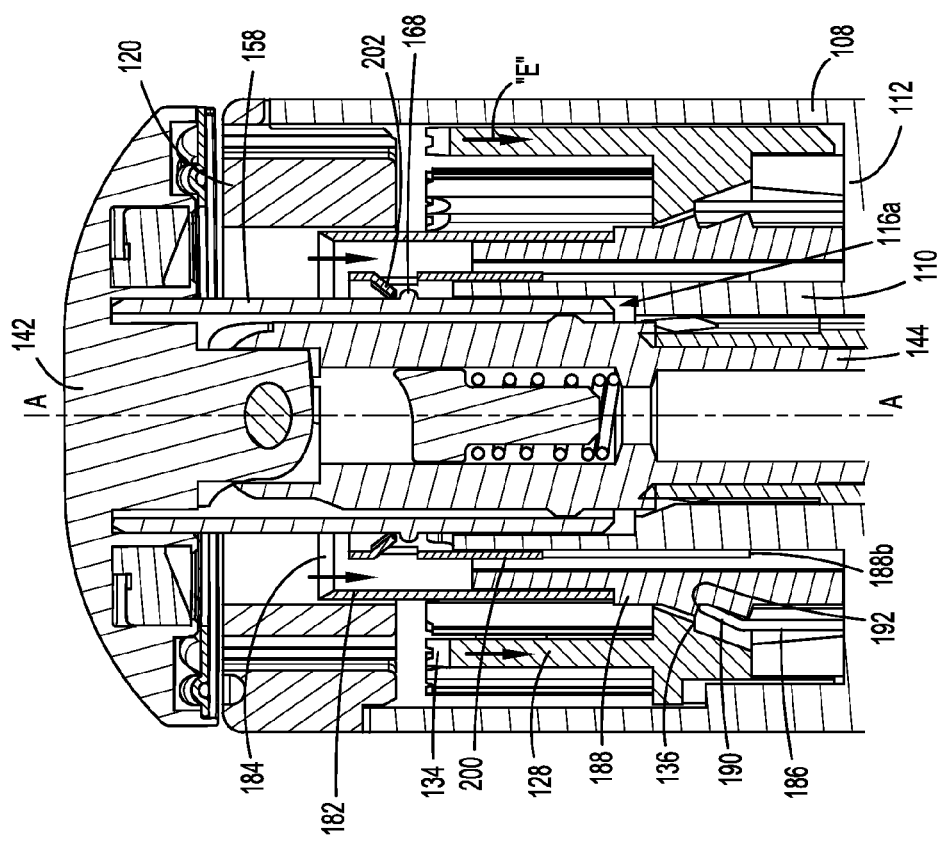
FIG. 15 is a side, cross-sectional view of the anvil assembly and cartridge assembly of FIG. 14A, illustrating the locking sleeve secured to the sliding sleeve after the second stroke.

With reference now to FIG. 15, after knife blade 182 severs upper and lower tissue portions "$T_U$" and "$T_L$" (FIGS. 16 and 17) and locking sleeve 200 engages sliding sleeve 158, drive member 104 is once again retracted in the direction indicated by arrows "E". As drive member 104 is once again retracted, staple pusher 128 and knife pusher 186 are also retracted as described above during the first stroke. As staple pusher 128 retracts in the direction indicated by arrows "E", flange 136 engages outer lip 192 of knife carrier 188 to drive knife carrier 188 in the direction indicated by arrows "E" to return knife carrier 188 and knife blade 182 to the initial position. Locking sleeve 200 remains in place engaged to sliding sleeve 158 to retain sliding sleeve 158 within cartridge assembly 102. As discussed above, locking sleeve 200 is also retained in cartridge assembly 102 by tab 204 (FIGS. 10A and 10B) of locking sleeve 200 engaging slot 118 (FIGS. 10A and 10B) of inner cylindrical portion 110.

Because circular stapler 10 uses separate strokes for forming staples 125 and cutting tissue, respectively, less force is required for the actuation of each stroke as compared to a conventional circular stapler including both staple ejecting/forming and tissue cutting functions in a single stroke. In addition to the reduced force requirements provided by the two stroke operation of circular stapler 10, the independent or decoupled staple forming and tissue cutting function of circular stapler 10 also permits the varying of the staple crimp height relative to the knife travel distance, the varying of the staple travel speed relative to the knife travel speed, and provides the addition of a dwell time between staple formation and tissue cutting. This configuration allows a clinician to optimize staple crimp heights to given conditions, such as, tissue thickness, tissue compliance and clamping force. This configuration may also allow for the monitoring of staple forming and knife cutting forces to alert the clinician in case an abnormal force is detected. This configuration further allows force and other data to be monitored and used for data collection and research, which when analyzed, may lead to further optimization of operational parameters, such as staple crimp height, dwell time and/or travel speed. By independently controlling and optimizing these various stapling and cutting parameters, improved hemostasis and/or anastomonic joint strength may result across a much broader range of tissue thicknesses, thereby allowing a clinician to have improved and customized control over the results.

With reference now to FIGS. 16, 17 and 18, after the second stroke or cutting stroke, firing of the circular stapler 10 (FIG. 1) is complete and anvil assembly 140 is un-approximated relative to cartridge assembly 102 by actuation of adjustment knob 18. During un-approximation, tab 204 (FIGS. 10A and 10B) of locking sleeve 200 engages distal end 118a of slot 118 (FIGS. 10A and 10B) to retain locking sleeve 200, and sliding sleeve 158, within cartridge assembly 102. Sliding sleeve 158 is retained within cartridge assembly 102 due to flange portion 202 of locking sleeve 200 engaging nubs 168 of sliding sleeve 158.

Since locking sleeve 200 retains sleeve 158 within cartridge assembly 102, the distal end 160 of sliding sleeve 158 is withdrawn from recess 162 of anvil head 142, thereby allowing anvil head 142 to tilt relative to anvil shaft 144 due to the biasing force of spring 152. In addition, since sliding sleeve 158 is retained within cartridge assembly 102, the anastomosis donut "D" coaxially disposed about sliding sleeve 158 is also retained within cartridge assembly 102, as seen in FIG. 16, and anvil head 142 can tilt relative to anvil shaft 144 without pinching or engaging the anastomosis donut "D". This ensures that anvil head 142 can reach the fully tilted position for withdrawal through anastomosis, and unnecessary damage to the anastomosis can therefore be reduced. In addition, once circular stapler 10 (FIG. 1) has been withdrawn from anastomosis, the surgeon may remove anvil assembly 140 and the anastomosis donut "D" from cartridge assembly 102 and inspect the anastomosis donut "D" to ensure that the anastomosis has been properly formed, as illustrated in FIGS. 18A and 18B.

With reference to FIGS. 19-26, in an alternative embodiment of the present disclosure, circular stapler 10 (FIG. 1) includes a cartridge assembly 302 and an anvil assembly 340. Cartridge assembly 302 and anvil assembly 340 are substantially similar to cartridge assembly 102 and anvil assembly 140 and will only be described as relates to the difference therebetween.

With particular reference to FIGS. 19-22, anvil assembly 340 includes a tilt-able anvil head 342 similar to anvil head 142. Anvil assembly 340 also includes a sliding sleeve 358 having a lip 364 at a distal end 360 and a flanged portion 368 at a proximal end 366. Distal end 360 of sliding sleeve 358 engages anvil head 342 to maintain anvil head 342 in the un-tilted condition. Flanged portion 368 includes a radially inward depending or extending nub 369 configured for engaging a recess 345 of anvil shaft 344 to removably couple sliding sleeve 358 to anvil shaft 344 and anvil assembly 340. In this way sliding sleeve 358 is removably fixed to anvil shaft 344 and translates with anvil assembly 340 relative to cartridge assembly 302 during approximation of anvil assembly 340 relative to cartridge assembly 302. Shaft 344 is removably insertable into a central bore 316 (FIG. 22C) of cartridge assembly 302.

With reference now to FIGS. 20 and 22A-22C, cartridge assembly 302 includes a housing 306, a staple cartridge 320 and a staple pusher 328. Housing 306 includes an outer shaft portion 308, an inner shaft portion 310, and supports or ribs 312, similar to housing 106 above. In this embodiment, housing 306 defines a substantially conical shape. It is contemplated that housing 306 may alternatively have a cylindrical shape, similar to housing 106 above. As described above with respect to staple pusher 128, staple pusher 328 is slidably and coaxially mounted in a channel 314 defined between outer and inner cylindrical portions 308 and 310 of housing 306 respectively. In this embodiment, staple pusher 328 is operatively coupled to the drive assembly (not shown) and is configured to both eject/form staples 124 and also to drive knife assembly 380 to sever tissue in a single stroke. It is contemplated, however that cartridge assembly 302 may alternatively be configured to include separate staple ejecting/forming and tissue cutting components similar to those described with respect to cartridge assembly 102 for ejecting/forming staples 124 and driving knife assembly 380 to sever tissue in separate strokes.

Figure 20:
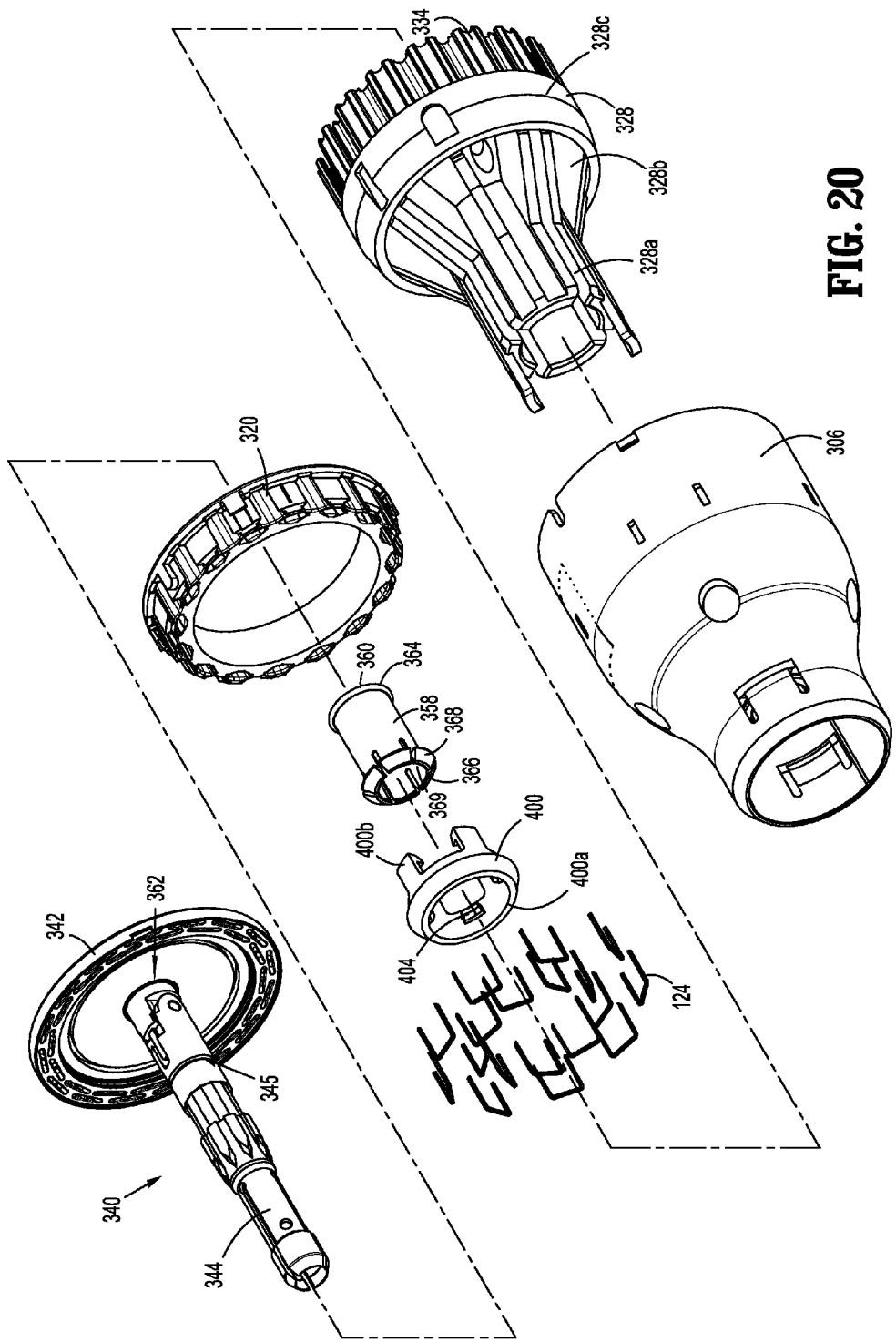
FIG. 20 is an exploded perspective view of the cartridge assembly and anvil assembly of the circular stapler of FIG. 19.
Figure 22C:
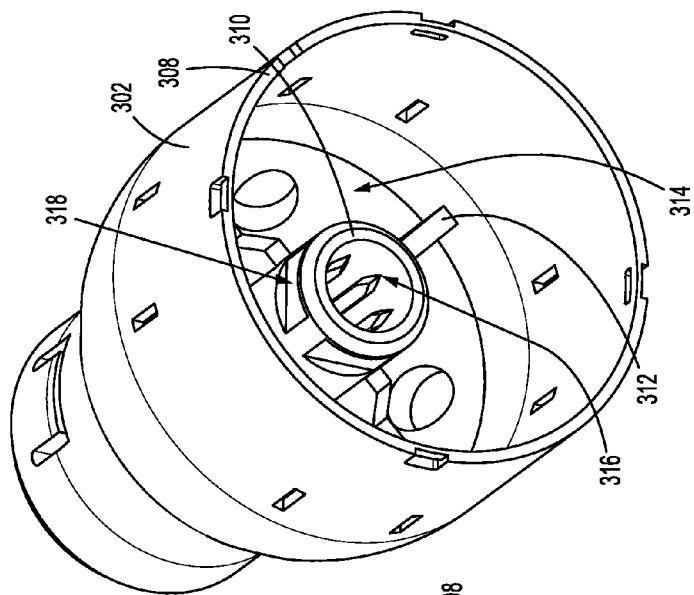
FIG. 22C is a top, perspective view of the housing of FIG. 22A.
Figure 22B:
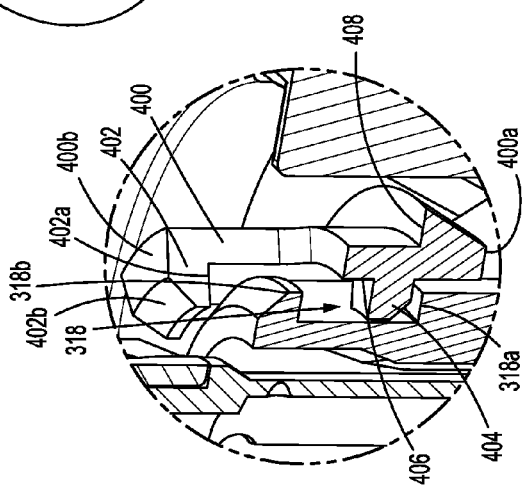
FIG. 22B is a perspective, cross-sectional view of the area of detail depicted in FIG. 22A, illustrating the protrusion of the locking sleeve disposed in the slot of the inner shaft portion of the housing.
Figure 22A:
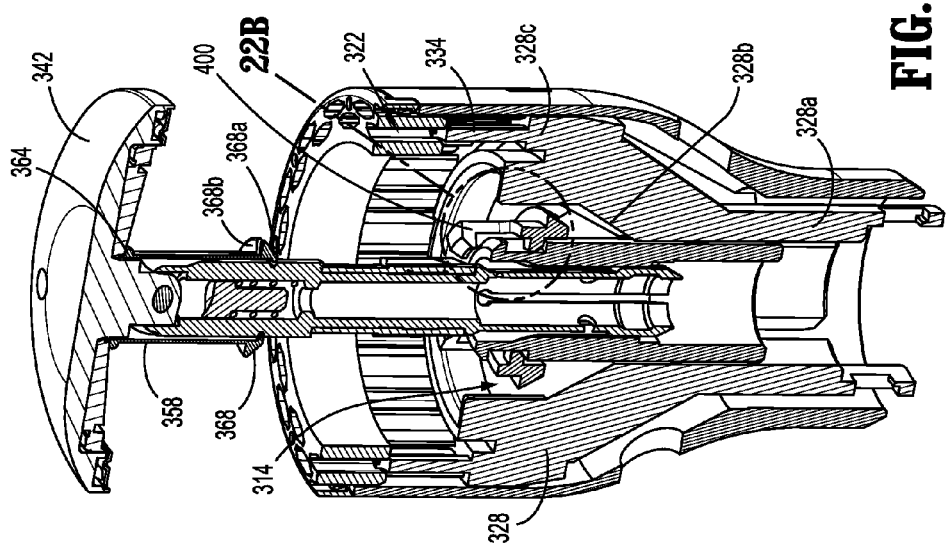
FIG. 22A is a perspective, cross-sectional view of the anvil assembly and cartridge assembly of FIG. 19, illustrating the anvil assembly un-approximated relative to the cartridge assembly.

With reference now to FIGS. 20 and 22A, staple pusher 328 includes a proximal portion 328a, an intermediate portion 328b and a distal portion 328c. Proximal portion 328a of staple pusher 328 is configured for insertion into channel 314 of housing 306 adjacent inner shaft portion 310 at a proximal portion of cartridge assembly 302. Intermediate portion 328b of staple pusher 328 defines a generally radially outward taper extending toward outer shaft portion 308. Distal portion 328c of staple pusher 328 includes fingers 334 for engaging staples 124 to drive staples 124 out of staple receiving slots 322.

Figure 21A:
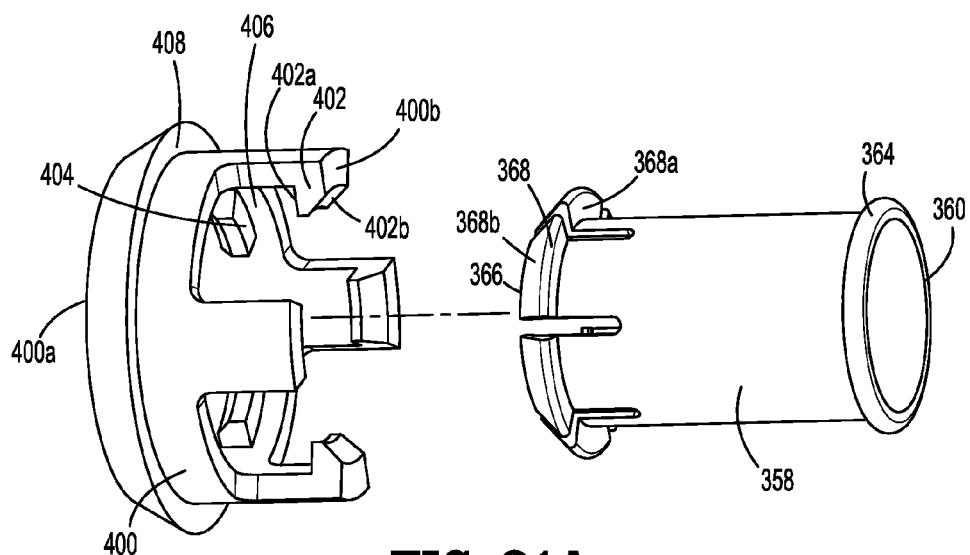
FIG. 21A is a perspective view of the sliding sleeve and locking sleeve of FIG. 20.

With reference now to FIGS. 20-22, cartridge assembly 302 includes a locking sleeve 400 defining a proximal end 400a and a distal end 400b. Locking sleeve 400 is coaxially disposed about inner shaft portion 310 and includes protrusions 404 on an inner surface 406 which are configured to slidably engage slots 318 disposed on an outer surface of inner shaft portion 310. Slots 318 of inner shaft portion 310 include proximal and distal ends 318a and 318b, respectively, which define a pathway therebetween along which protrusions 404 of locking sleeve 400 may travel. Locking sleeve 400 includes a lip 408 proximate to proximal end 400a which tapers inwardly from distal to proximal. Intermediate portion 328b of staple pusher 328 is configured to engage lip 408 to drive locking sleeve 400 distally when staple pusher 328 is driven distally during the first and/or second stroke. Distal end 400b of locking sleeve 400 includes flange portions 402 configured to engage flanged portion 368 of sliding sleeve 358. Flange portions 402 of locking sleeve 400 define a first proximal surface 402a and a second distal surface 402b. First proximal surface 402a is substantially perpendicular to inner shaft portion 310 and is configured to engage a corresponding distal surface 368a of flanged portion 368 of sliding sleeve 358. Second distal surface 402b is tapered or offset at an angle to first proximal surface 402a and is configured to slidably engage and snap over a tapered or angled portion 368b of flanged portion 368.

Figure 23B:
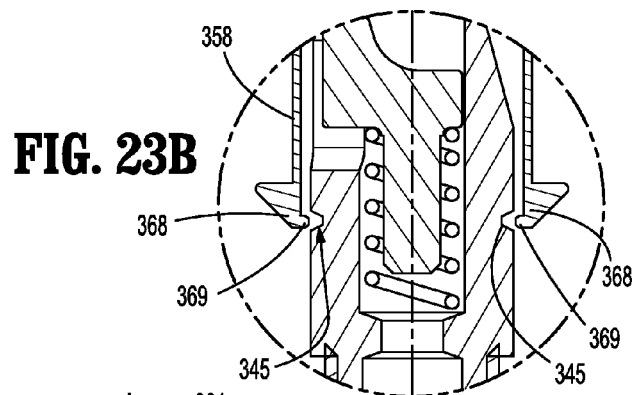
FIG. 23B is a side, cross-sectional view of the area of detail depicted in FIG. 23A, illustrating nubs of the sliding sleeve engaging a recess in the anvil shaft.
Figure 23A:
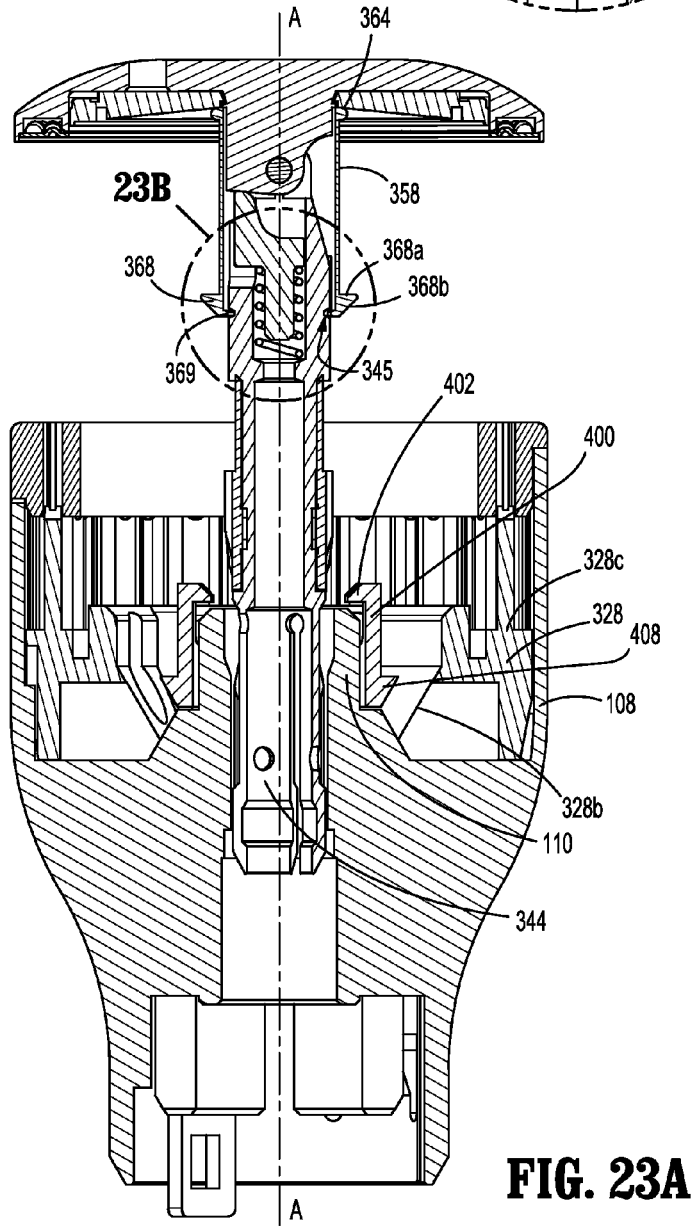
FIG. 23A is a side, cross-sectional view of the anvil assembly and cartridge assembly of FIG. 22A, illustrating the anvil assembly un-approximated relative to the cartridge assembly.
Figure 24:
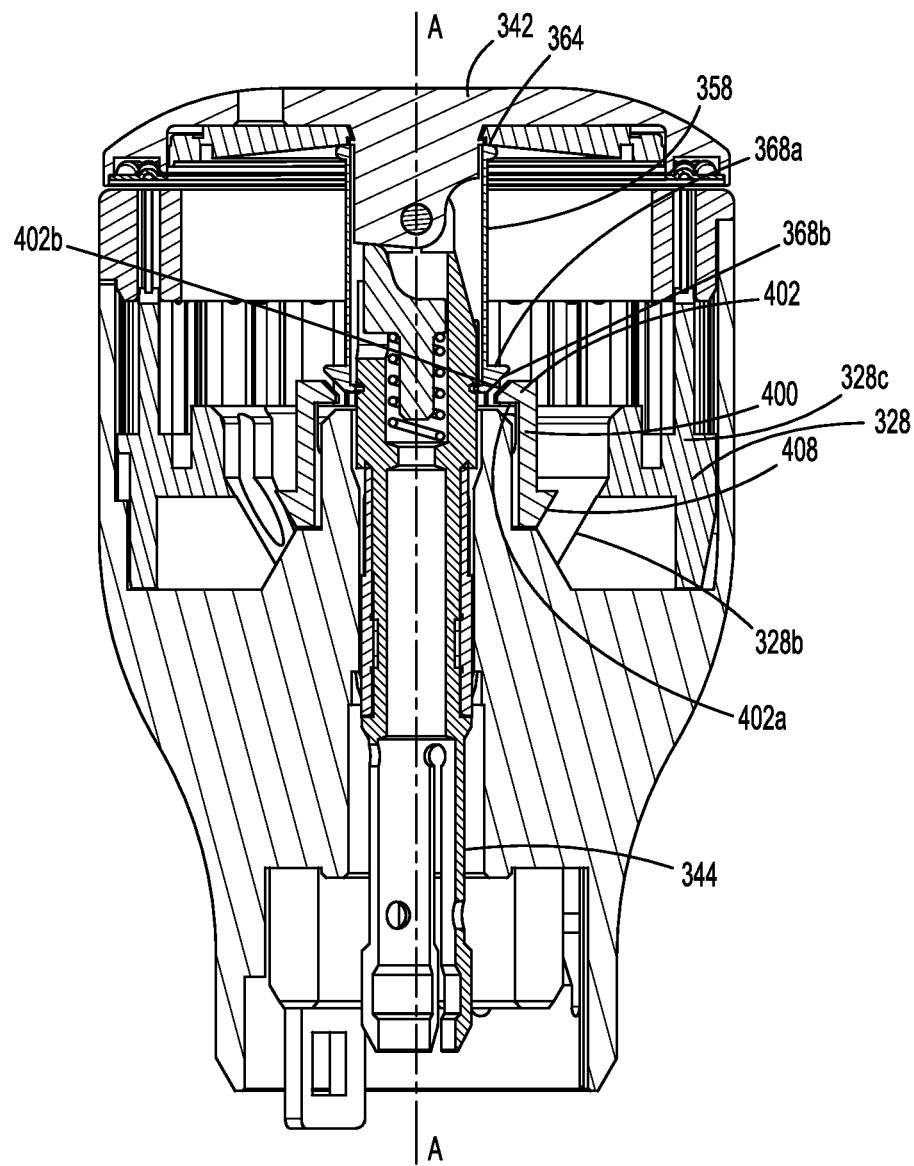
FIG. 24 is a side, cross-sectional view of the anvil assembly and cartridge assembly of FIG. 23A, the anvil assembly approximated relative to the cartridge assembly.

With reference now to FIGS. 19 and 23-26, the operation of circular stapler 10, including cartridge assembly 302 and anvil assembly 340, will now be described. Referring initially to FIG. 23, in an initial condition anvil assembly 340 is un-approximated relative to cartridge assembly 302 with staple pusher 328 and locking sleeve 200 at their respective proximal most positions. With reference to FIG. 24, anvil assembly 340 is then approximated relative to cartridge assembly 302 such that proximal end 366 of sliding sleeve 358 is disposed proximate to distal end 310a of inner shaft portion 310. As described above, when anvil assembly 340 is approximated relative to cartridge assembly 302, upper and lower portions of tissue "$T_U$" and "$T_L$" are grasped therebetween.

Figure 21B:
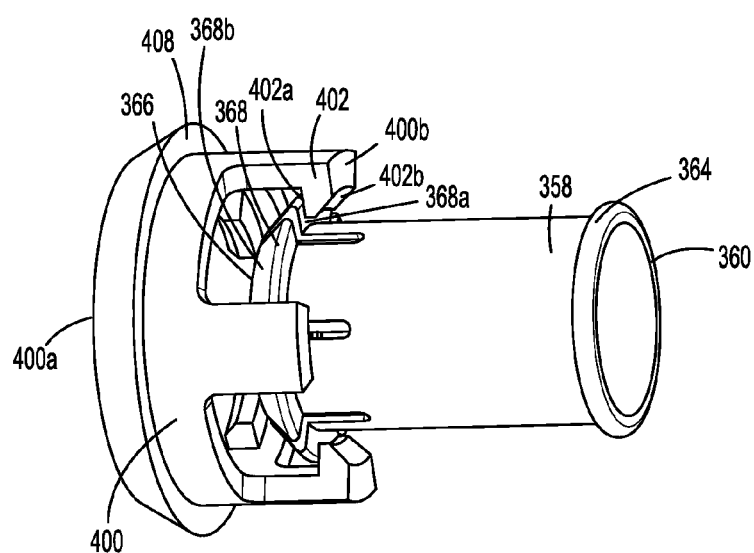
FIG. 21B is a perspective view of the sliding sleeve and locking sleeve of FIG. 21A, illustrated the sliding sleeve engaged with the locking sleeve.
Figure 25:
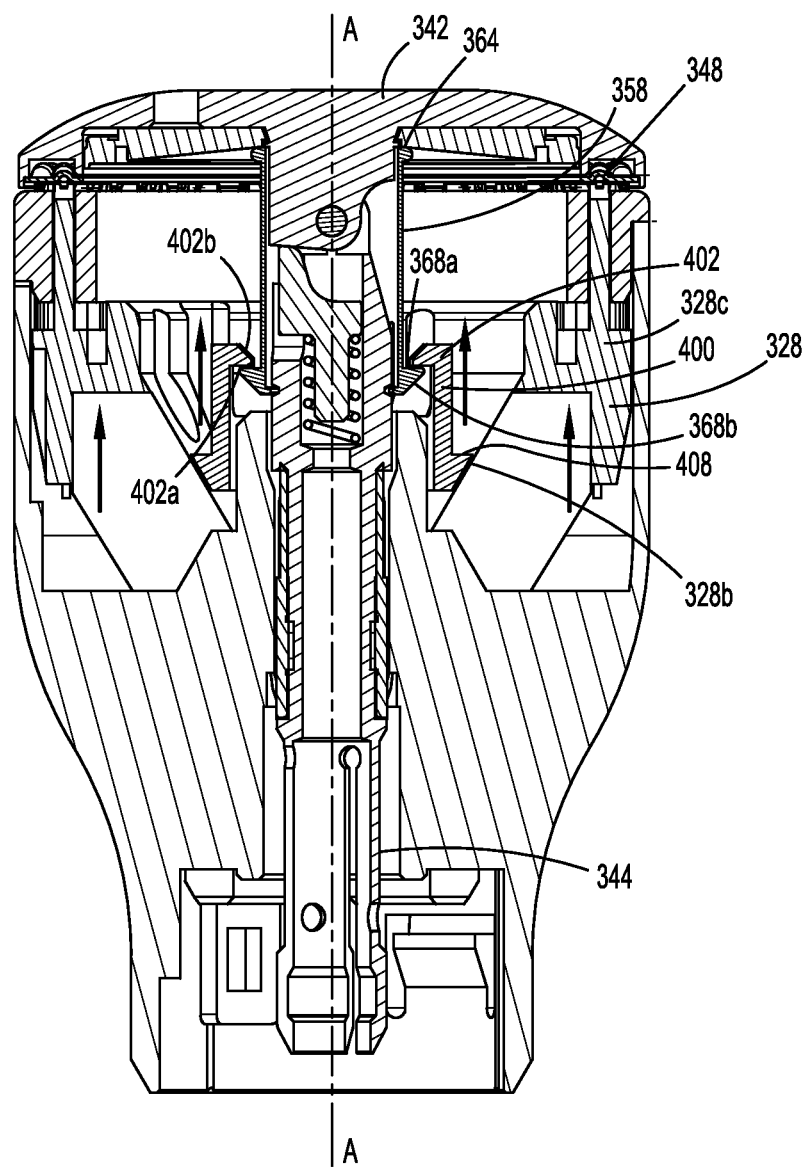
FIG. 25 is a side, cross-sectional view of the anvil assembly and cartridge assembly of FIG. 24, illustrating the firing stroke of the staple pusher.

Referring now to FIG. 25, during the first stroke, as described above, retraction or actuation of trigger 16 (FIG. 1) relative to handle 14 (FIG. 1) causes advancement of drive assembly (not shown) which operably engages staple pusher 328 to cause advancement of staple pusher 328 in the distal direction to eject/form staples 124 (FIG. 20) against staple forming pockets 348 of anvil head 342. During distal translation of staple pusher 328, intermediate portion 328b of staple pusher 328 engages lip 408 of locking sleeve 400 to thereby drive locking sleeve 400 distally. As locking sleeve 400 is driven distally, distal surfaces 402b of flange portions 402 engage and snap over tapered portion 368b of flanged portion 368 of sliding sleeve 358. Once flange portions 402 of locking sleeve 400 are engaged with flanged portion 368 of sliding sleeve 358, proximal surfaces 402a of flange portions 402 of locking sleeve 400 are engaged with distal surface 368a of flanged portion 368 of sliding sleeve 358 thereby securing sliding sleeve 358 to locking sleeve 400 (FIGS. 21B and 25). When staple pusher 328 is retracted, locking sleeve 400 remains in place securing sliding sleeve 358.

Figure 26A:
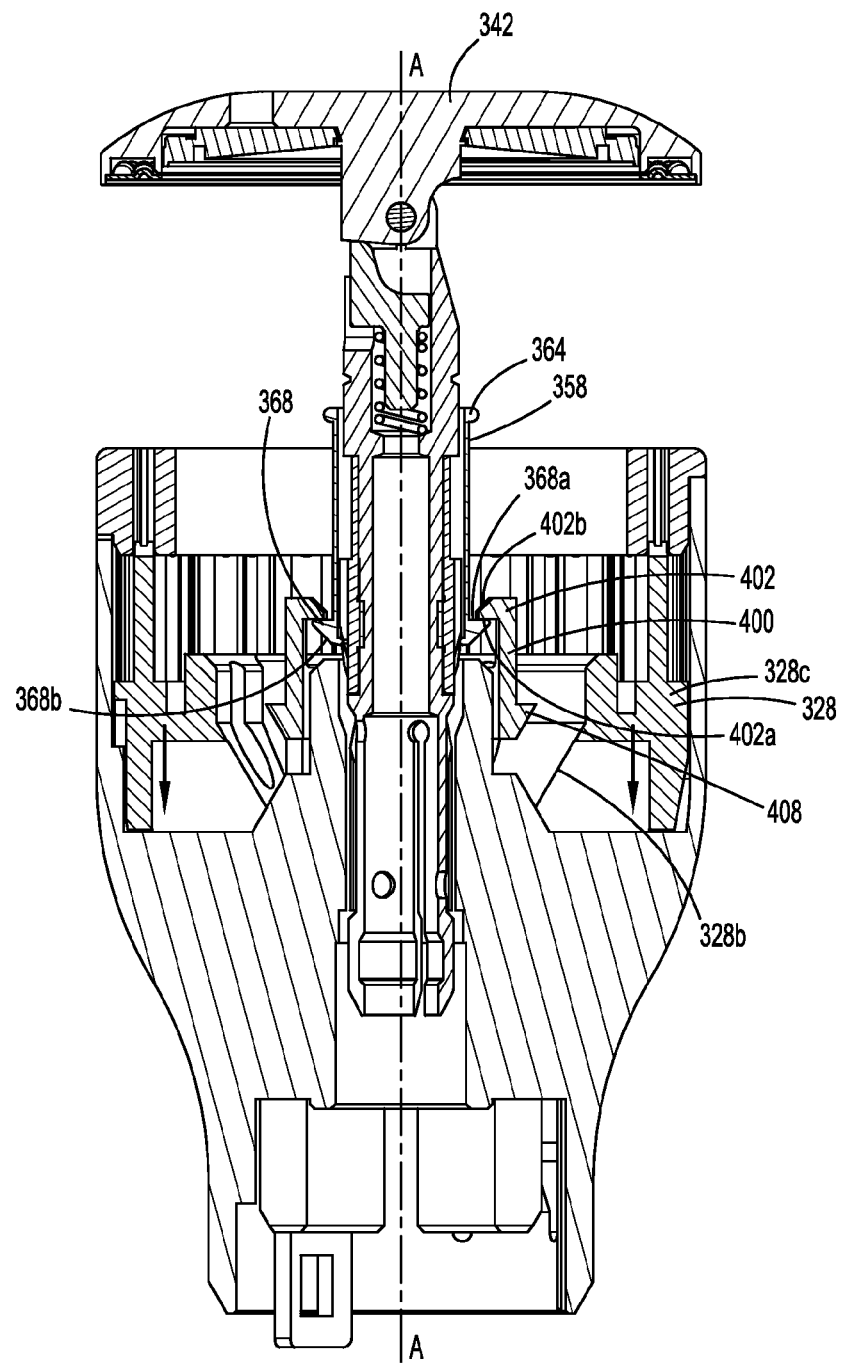
FIG. 26A is a side, cross-sectional view of the anvil assembly and cartridge assembly of FIG. 25 after firing is complete, illustrating the sliding sleeve being retained in the cartridge assembly by the locking sleeve after the anvil assembly has been un-approximated relative to the cartridge assembly.
Figure 26B:
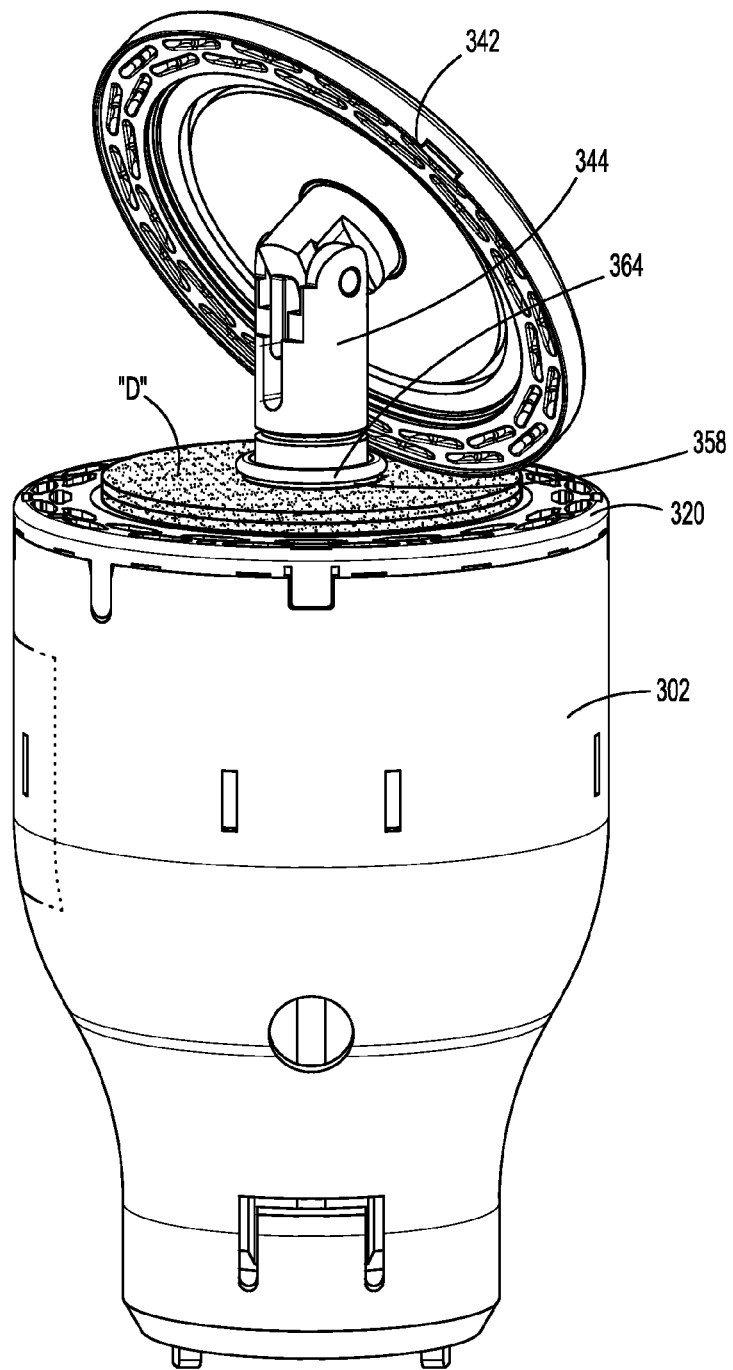
FIG. 26B is a perspective view of the anvil assembly and cartridge assembly of FIG. 26A, illustrating the anastomosis donut retained by the sliding sleeve and the anvil head in the tilted condition.
Figure 26C:
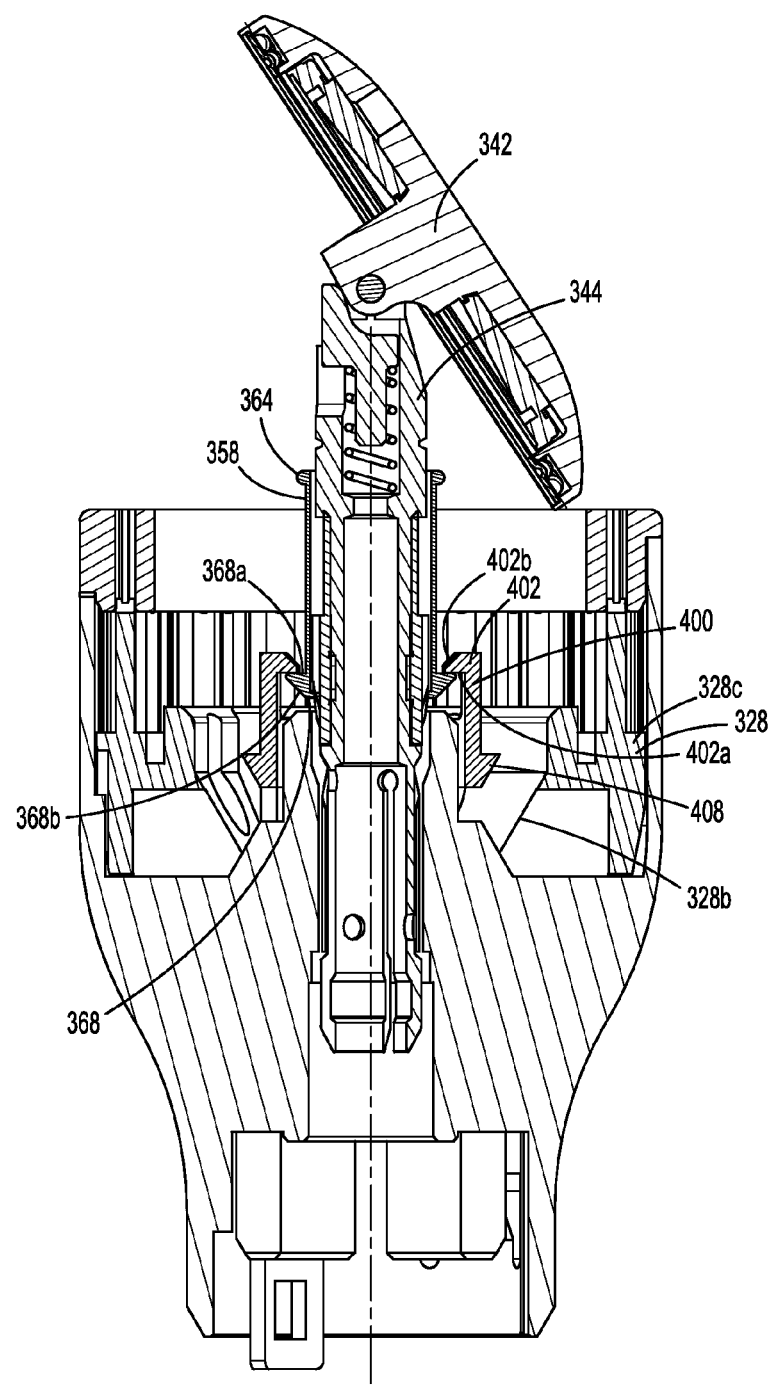
FIG. 26C is a side, cross-sectional view of the anvil assembly and cartridge assembly of FIG. 26B.

Referring now to FIGS. 26A-26C, after firing is complete, anvil assembly 340 is un-approximated relative to cartridge assembly 302. During un-approximation of anvil assembly 340, sliding sleeve 358 and anastomosis donut "D" are retained in cartridge assembly 302 due the engagement of locking sleeve 400 with sliding sleeve 358 and distal end 360 of sliding sleeve 358 is disengaged from anvil head 342. Lip 364 assists in retaining anastomosis donut "D" in with sliding sleeve 358. Anvil head 342 is now free to tilt (FIGS. 26B and 26C) as described above and the circular stapler 10 (FIG. 1) may be withdrawn from the anastomosis.

It is contemplated that individual features of the above described embodiments may be combined without departing from the scope of the present disclosure. For example, any of the above embodiments may include the necessary structures or elements to perform either single stroke staple/forming and cutting or separate multi-stroke staple forming and cutting while still utilizing the appropriate locking member and sliding sleeve. In addition, any of the above embodiments may alternatively include a powered actuation system as described above.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A surgical stapling device for joining tissue portions, comprising:
   a handle assembly;
   an elongate body extending from the handle assembly;
   a cartridge assembly supported on a distal end of the elongate body, the cartridge assembly including a staple cartridge containing a plurality of surgical staples in an annular array;
   an anvil assembly at a distal end of the surgical stapling device, the anvil assembly having a shaft for removably coupling the anvil assembly to the cartridge assembly and a head pivotally mounted to a distal end of the shaft, the anvil assembly translatable relative to the cartridge assembly between a first position, where the anvil assembly is spaced from the cartridge assembly, and a second position, where the anvil assembly is approximated relative to the cartridge assembly for clamping tissue therebetween, the head of the anvil assembly transitionable between a first condition, where a tissue contacting surface of the head is substantially perpendicular to the shaft, and a second condition, where the tissue contacting surface of the head is tilted relative to the shaft; and a sleeve member slidably disposed about the shaft of the anvil assembly, the sleeve member transitionable between a first position, where the sleeve member engages the head of the anvil assembly to secure the head in the first condition, and a second position, where the sleeve member is disengaged from the head of the anvil assembly to allow the head to transition to the second condition.

2. A surgical stapling device according to claim 1, wherein a distal end portion of the sleeve member is insertable into a recess of the head of the anvil to removably couple the sleeve member to the anvil assembly and secure the head in the first condition.

3. A surgical stapling device according to claim 1, wherein the cartridge assembly includes a locking member, the locking member translatable relative to the sleeve member to engage a protrusion of the sleeve member when the anvil assembly is in the second position, the locking member configured to axially maintain the sleeve member relative to the cartridge assembly and to disengage the sleeve member from the head of the anvil assembly when the anvil assembly transitions from the second position to the first position.

4. A surgical stapling device according to claim 3, wherein the cartridge assembly includes a knife carrier, the knife carrier translatable relative to the cartridge assembly to engage and translate the locking member relative to the sleeve member.

5. A surgical stapling device according to claim 4, wherein the cartridge assembly includes a knife pusher, the knife pusher configured to engage a lip of the knife carrier and translatable relative to the cartridge assembly to translate the knife carrier relative to the cartridge assembly.

6. A surgical stapling device according to claim 5, wherein the knife pusher is configured to translate relative to the cartridge assembly during actuation of a first stroke of the surgical stapling device, with the knife pusher disengaged from the lip of the knife carrier, and configured to translate relative to the cartridge assembly during actuation of a second stroke of the surgical stapling device, with the knife pusher engaged with the lip of the knife carrier, to thereby translate the knife carrier relative to the cartridge assembly during the second stroke.

7. A surgical stapling device according to claim 1, wherein the sleeve member is configured to retain a severed donut of tissue thereabout after actuation of the surgical stapling device.

8. A surgical stapling device for joining tissue portions, comprising:
a handle assembly;
an elongate body extending from the handle assembly;
a cartridge assembly supported on a distal end of the elongate body, the cartridge assembly including a staple cartridge containing a plurality of surgical staples in an annular array;
an anvil assembly at a distal end of the surgical stapling device, the anvil assembly having a shaft for removably coupling the anvil assembly to the cartridge assembly and a head pivotally mounted to a distal end of the shaft, the anvil assembly translatable relative to the cartridge assembly between a first position, where the anvil assembly is spaced from the cartridge assembly, and a second position, where the anvil assembly is approximated relative to the cartridge assembly for clamping tissue therebetween, the head of the anvil assembly transitionable between a first condition, where a tissue contacting surface of the head is substantially perpendicular to the shaft, and a second condition, where the tissue contacting surface of the head is tilted relative to the shaft; and
a staple pusher slidably disposed within the cartridge assembly and configured to translate relative to the cartridge assembly to engage the plurality of surgical staples and urge the plurality of surgical staples towards the anvil assembly;
a sleeve member slidably disposed about the shaft of the anvil assembly, the sleeve member transitionable between a first position, where the sleeve member engages the head of the anvil assembly to secure the head in the first condition, and a second position, where the sleeve member is disengaged from the head of the anvil assembly to allow the head to transition to the second condition; and
a locking member slidably disposed within the cartridge assembly, the locking member translatable relative to the sleeve member upon translation of the staple pusher relative to the cartridge assembly, the locking member configured to engage the sleeve member to axially maintain the sleeve member relative to the cartridge assembly and to disengage the sleeve member from the head of the anvil assembly when the anvil assembly transitions from the second position to the first position.

9. A surgical stapling device according to claim 8, wherein a proximal end of the locking member defines a sloped surface, the sloped surface of the locking member configured to engage a corresponding sloped surface of the pusher upon translation of the pusher relative to the cartridge assembly to translate the locking member relative to the sleeve member.

10. A surgical stapling device according to claim 8, wherein the sleeve member includes a flanged portion at a proximal end.

11. A surgical stapling device according to claim 10, wherein a distal end of the locking member includes a flanged portion, the flanged portion of the locking member configured to engage the flanged portion of the sleeve member upon translation of the locking member relative to the sleeve member.

12. A surgical stapling device according to claim 8, wherein a distal end of the sleeve member includes a lip, the lip configured to engage a recess in the head of the anvil assembly to removably secure the sleeve member to the anvil assembly.

13. A surgical stapling device according to claim 8, wherein a proximal end of the sleeve member includes a nub extending radially inward therefrom, the nub configured to engage a recess of the shaft.

* * * * *